United States Patent [19]

Parker et al.

[11] Patent Number: 5,099,848

[45] Date of Patent: Mar. 31, 1992

[54] METHOD AND APPARATUS FOR BREAST IMAGING AND TUMOR DETECTION USING MODAL VIBRATION ANALYSIS

[75] Inventors: Kevin J. Parker; Robert M. Lerner; Sung-Rung Huang, all of Rochester, N.Y.

[73] Assignee: University of Rochester, Rochester, N.Y.

[21] Appl. No.: 608,391

[22] Filed: Nov. 2, 1990

[51] Int. Cl.$^5$ .............................................. A61B 8/00
[52] U.S. Cl. ................................. 128/661.07; 73/575; 128/660.05; 128/774
[58] Field of Search ..................... 128/660.01, 660.05, 128/661.09, 774, 661.07; 73/575

[56] References Cited

U.S. PATENT DOCUMENTS

| | | | |
|---|---|---|---|
| Re. 32,782 | 11/1988 | Pratt, Jr. ............................. | 128/774 |
| 4,097,835 | 6/1978 | Green .................................. | 128/660.05 |
| 4,338,948 | 7/1982 | Perez-Mendez et al. ........ | 128/660.01 |
| 4,742,830 | 5/1988 | Tamano et al. ................... | 128/661.09 |
| 4,819,649 | 4/1989 | Rogers et al. .................... | 128/660.02 |
| 4,853,904 | 8/1989 | Pesque .............................. | 128/661.08 |

OTHER PUBLICATIONS

"Automated Noninvasive Motion Measurement of Auditory Organs in Fish Using Ultrasound" by Cox and Rogers, *Journal of Vibration, Acoustics, Stress, and Reliability in Design*, pp. 55-59, Jan. 1987.

"Absolute Calibration of Acoustic Sensors Utilizing Electromagnetic Scattering from in situ Particulate Matter", Pierce and Berthelot, presented to Session II. *Engineering Acoustics IV; Laboratory and Measurement Condenser Microphones*, May 1988.

"Imaging the Amplitude of Vibration Inside the Soft Tissues for Forced Low Frequency Vibration", Yamakoshi, Mori and Sato, *Japanese Journal of Medical Ultrasonics*, vol. 16, No. 3, 1989.

"Ultrasound Imaging of Internal Vibration of Soft Tissue Under Force Vibration", Yamakoshi, J. Sato and T. Sato, *IEEE Transactions on Ultrasonics, Ferroelectics and Frequency Control*, vol. 37, No. 2, pp. 45-53, Mar. 1990.

"A pulsed Doppler ultrasonic system for making noninvasive measurements of the mechanical properties of soft tissue", Krouskop, Dougherty and Levinson, *J. Rehabilitation Res. & Develop.*, vol. 24, No. 2, pp. 1-8, 1987.

"Ultrasonic study of in vivo kinetic characteristics of human tissues", Tristam, Barbosa, Cosgrove, Nassiri, Bamber and Hill, *Ultrasound in Med. & Biol.*, vol. 12, No. 13, pp. 927-937, 1986.

"Physics of vibrations in living tissues", Von Gierke, Oestreicher, Franke, Parrack and Von Wittern, *J. Appl. Physiol.*, vol. 4, pp. 886-900, Jun. 1952.

"Application of Fourier analysis to clinical study of patterns of tissue movement", Tristam, Barbosa, Cosgrove, Nassiri, Bamber and Hill, *Ultrasound in Med. & Biol.*, vol. 14, No. 8, pp. 695-707, 1988.

(List continued on next page.)

Primary Examiner—Francis Jaworski
Assistant Examiner—George Manuel
Attorney, Agent, or Firm—Dickstein, Shapiro & Morin

[57] ABSTRACT

A system for using Doppler modulation parameters for producing an estimation of the vibration amplitude of an object under investigation is disclosed in which a low frequency vibration source is used to force the oscillation of the object under investigation and a coherent or pulsed ultrasound imaging system is utilized to detect the spatial distribution of the vibration amplitude of the object in real-time. The reflected Doppler shifted waveform generated by reflecting the ultrasound waves off of the vibrating object under investigation is used to compute the vibration amplitude and frequency of the object using two alternative methods, either on a frequency domain estimator basis or on a time domain estimator basis. The system may also be utilized for breast imaging and tumor detection. By conforming the breast to a regular geometry, exciting specific vibrational eigenmodes, and analyzing the Doppler modulation parameters, the inherent shear and longitudinal wave parameters of breast tissue can be calculated. These are useful for detection of tumors and other abnormalities.

32 Claims, 15 Drawing Sheets

OTHER PUBLICATIONS

"Ultrasonic measurement of small displacements and deformations of tissues", Wilson and Robinson, *Ultrasonic Imaging*, vol. 4, pp. 71-82, Academic Press, Inc. (1982).

"Tissue characterization by quasi-real time mapping of internal movement using forced vibration", Uamakoshi, Sato and Sato, in M. Linzer ed., *Ultrasonic Imaging*, vol. 11, *Abstracts, 14th International Symposium on Ultrasonic Imaging and Tissue Characterization*, Jun. 5-7, 1989, Arlington, VA, Academic Press, Inc., New York.

"Representations of rapidly oscillating structures on the Doppler display", Holen, Waag and Gramiak, *Ultrasound in Med. & Biol.*, vol. 11, No. 2, pp. 267-272, 1985.

"Sono-Elasticity: Medical Elasticity Images Derived from Ultrasound Signals in Mechanically Vibrated Targets", *Acoustical Imaging*, vol. 16; Robert M. Lerner, Kevin J. Parker, Jarle Holen, Raymond Gramiak and Robert C. Wang, ed.; L. W. Kessler, Plenum Publishing Corp. (1988).

"Sono-Elasticity: Medical Elasticity Images Derived from Ultrasound Signals in Mechanically Vibrated Targets", Robert M. Lerner, Kevin J. Parker, Jarle Holen, Raymond Gramiak and Robert C. Wang to appear in: Ultrasonic Tissue Characterization and Echographic Imaging 7, Proceedings of the Seventh European Communities Workshop; Nikmegen, The Netherlands.

*Ultrasound in Medicine and Biology*, vol. 16, No. 3, pp. 231-239; "Sonoelasticity Images Derived from Ultrasound Signals in Mechanically Vibrated Tissues" by Robert M. Lerner, S. R. Huang and Kevin J. Parker.

*Ultrasound In Medicine and Biology*, vol. 16, No. 3, pp. 241-246; "Tissue Response to Mechanical Vibrations for Sonoelasticity Imaging" by K. J. Parker, S. R. Huang, R. A. Musulin and R. M. Lerner.

$$w_3 = \cos^2\left(\frac{\omega_L T_s}{2}\right)\left[4\sin^2(\omega_L T_s)\cos^2\left(\frac{\omega_L T_s}{2}\right)\right]^{-1}$$

$$w_4 = \sin^2\left(\frac{\omega_L T_s}{2}\right)\left[4\sin^2(\omega_L T_s)\cos^2\left(\frac{\omega_L T_s}{2}\right)\right]^{-1}$$

METHOD AND APPARATUS FOR BREAST IMAGING AND TUMOR DETECTION USING MODAL VIBRATION ANALYSIS

CROSS-REFERENCE TO RELATED APPLICATION

This application is related to United States patent application Ser. No. 07/608,389, filed concurrently herewith, and entitled METHOD AND APPARATUS FOR USING DOPPLER MODULATION PARAMETERS FOR ESTIMATION OF VIBRATION AMPLITUDE, which is commonly assigned.

BACKGROUND OF THE INVENTION

The present invention relates generally to the use of low frequency vibrations to investigate passive objects. More particularly, the present invention relates to a method of and a system for using low frequency vibrations to vibrate an object and then using high frequency wave energy reflected by an object for analyzing the vibration of the object created by the generated low frequency vibrations in order to examine the surface or cross-section of the object and to produce an image of the examined object. The pattern of vibrations produced in breast tissue and in other organs, measured as a function of position within the tissue and as a function of vibration frequency, are utilized to determine the elastic constants of the tissue.

It is frequently useful to examine passive structures or objects by means of the application of a swept frequency vibration or audio source. Structures which are typically examined in that manner for flaws include aircraft, ships, bridge trusses and other types of large structures. In addition, soft tissue can also be examined in that manner.

In the examination of such structures, the vibration sources may be temporarily mounted on exterior surfaces of, for example, ship hulls or bridge trusses, or may be placed in the interior of the structures to be examined, such as ship hulls or passenger aircraft. The interrogating wave energy is then focused on a reference point on or within the object.

Such interrogating wave energy may vary from a laser, microwave or airborne source, for use with aircraft, bridges, ships or other structures. Sonar or ultrasound sources may be utilized for underwater inspection. The vibration source of low frequency is swept over a broad frequency range so as to excite eigenmodes with relatively high vibrational amplitudes. Once an appropriate vibration frequency is found, the interrogating wave energy can then be scanned over the surface or within a cross-section of the interior for penetrating waves. The spot size or spatial resolution of the scan, depends upon the wavelength of the vibration source used and the particular apparatus used. For simply focused coherent sources, the spot size will be equal to (1.2)(wavelength) (focal length)/(aperture radius).

Since sub-millimeter wavelengths can be achieved by the instant invention using ultrasound and optical devices as interrogating wave sources, millimeter scale, spatial resolution can be achieved utilizing the present invention. Once an appropriate scan size or region of interest is selected, an image is derived from point-by-point examination of the Doppler shift of the reflection of the interrogating source back from the object. Although different prior techniques have been described which analyze vibrations using lasers or ultrasound, none of those techniques make use of externally applied vibration and point-by-point scanning using the method of the present invention, to generate a vibration image.

The method of the present invention is useful to generate an image whose intensity or color is proportional the vibration amplitude calculated by means of the inventive method, at each point on the object. That image can be inspected for modal shapes and abnormally high or low vibration amplitudes, and can also be compared with reference images obtained earlier or from well characterized analogous structures. In addition, the modal shapes at different frequencies can be analyzed to determine the elastic constants of the material. The time required for analysis of each spot utilizing the inventive method and system described herein is less than three cycles of the vibration frequency when the frequency domain estimator method is utilized and a fraction of a single vibration cycle if the time domain estimator method is utilized. Thus, those methods can be applied rapidly so as to permit real-time imaging. Because the methods are also sensitive to vibration but are stable in the presence of noise, vibrational amplitudes of less than 1/10 of a wavelength of the interrogating wave energy can be easily detected utilizing the inventive method and system.

One prior art approach to measuring amplitudes of vibration is shown in U.S. Pat. No. 4,819,649, issued Apr. 11, 1989, to Rogers et al. That patent is directed to a non-invasive vibration measurement system and method for measuring the acoustically induced vibrations within a living organism. That patent utilizes a continuous wave of high spectral purity ultrasonic beams and utilizes two separate transducers, one for transmitting and one for receiving the focused beams.

By virtue of its frequency domain processing, the device disclosed by Rogers et al. cannot produce real-time imaging. In fact, the '649 patent does not discuss imaging at all. All of the specific implementations discussed in the '649 patent relate to frequency domain techniques which are based upon the ratio of harmonic sidebands of the reflected signal, which allows the intrusion of noise elements into the reflected sample and, thus, into any analyzed signal.

The system and method disclosed in the '649 patent is also discussed in an article written by the inventors which appeared in the *Journal of Vibration. Acoustics, Stress and Reliability in Design*, entitled "Automated Non-Invasive Motion Measurement of Auditory Organs in Fish Using Ultrasound", Vol. 109, January 1987, pp. 55–59. That paper discloses the use of external vibration to produce an FM Doppler shift and examines, over long periods of time, the Doppler spectrum returning from a single point. It is not a real-time system. The article assumes that, using very small vibrations, the ratio of the carrier signal to the first harmonic is indicative of the vibration amplitude. Like the '649 patent, the device of Rogers and Cox disclosed in this paper is a non-scanning, slow, frequency domain method which uses the ratio of harmonic sidebands and is restricted to use with very low amplitudes.

Another approach used in the past is disclosed in an article entitled "Imaging the Amplitude of Vibration Inside the Soft Tissues for Forced Low Frequency Vibration", by Yamakoshi, Mori and Sato, published in the *Japanese Journal of Medical Ultrasonics*, Vol. 16, No. 3, pp. 221–229 (1989). That article discusses an imaging system which can observe the precise movements inside of soft tissues when an external vibration is applied to those tissues. While the system described in that article does scan and make vibration images, it uses frequency domain techniques which are also based on the ratio of harmonic sidebands approach which are noise sensitive. Furthermore, it is slow and not a practical real-time system and is restricted to use with small amplitudes of vibration.

Yet another approach used in the prior art is that of Pierce and Berthelot, as disclosed in *Proceedings of the SPIE*, Session EE. Engineering Acoustics IV: "Laboratory and Measurement Microphone", "Absolute Calibration of Acoustic Sensors Utilizing Electromagnetic Scattering from In Situ Particulate Matter", Pierce and Yves (1988). That paper describes the same FM Doppler spectrum utilized by Cox and Rogers and as described in their article discussed above. However, Pierce et al. utilize laser methods to measure the oscillation at a point. The methodology of Pierce et al. is a non-scanning, slow, frequency domain technique which again uses the ratio of harmonic sidebands and therefore suffers from the same noise sensitivity problems as do the other prior systems discussed above.

All of the known techniques can be broadly classified as utilizing the same approach to the estimation or determination of the vibrational parameters, that is, using some ratio of spectral harmonic amplitudes. Thus, they all suffer from the disadvantages of the ratio methods because they require either intensive computation or larger lookup tables of theoretical Bessel functions for comparison with the measured data. Further, ratio methods work well only when the argument of the Bessel function is small, which poses a severe limitation on the range of the estimation of the Doppler spectrum.

As a practical matter, the performance of the ratio methods is highly degraded since almost all Doppler spectra suffer from a poor signal-to-noise ratio. Additionally, a sophisticated algorithm is required to determine the best selection of the harmonic pair to be compared. The present invention, on the other hand, utilizes a simple and noise-immune method for vibration estimation or determination.

The present invention may also be utilized with soft tissue structures, such as for breast imaging or the imaging of tumors. The criterion of digital palpation for detecting such soft tissue abnormalities, namely "stiffness" or "hardness" of a "lump", is not directly related to either the ultrasound, x-ray or MRI appearance of a hard lesion. That is because stiffness refers to solid mechanical properties measured at constant or slowly varying force. However, ultrasound echogenicity relates to inhomogeneties in structure, as measured using frequency pressure waves. X-ray absorbtion is related to the density and the presence of high atomic number elements such as calcium. In magnetic resonance imaging, the image brightness is related to the proton density and spin-spin and spin-lattice relaxation processes. Thus, no in vivo modality is available which directly assesses the stiffness of a region of tissue. The instant invention directly assesses some mechanical properties of tissue and the presence of stiff inhomogeneties can be detected using low frequency vibration and the disclosed novel imaging and analysis techniques.

SUMMARY AND OBJECTS OF THE INVENTION

In view of the foregoing, it should be apparent that there still exists a need in the art for a method of and system for providing for the remote inspection of structures or soft tissues using an externally applied vibration source and which provides for the generation in real-time of an analysis of the returned signal from the object under investigation for Doppler shift properties. It is, therefore, a primary object of this invention to provide a method of and system for remotely inspecting structures and soft tissues using externally applied vibration and Doppler shift measurement which is characterized by providing an analysis on a real-time basis of the return signal of an interrogating wave for Doppler shift properties.

More particularly, it is an object of this invention to provide a remote inspection system as aforementioned which provides for an analysis of the Doppler shifted interrogation signal in order to derive the local vibration amplitude of the reflector or object under investigation as either a gray scale or color image.

Still more particularly, it is an object of this invention to provide a system for remotely inspecting objects in which the image which represents the analyzed Doppler shifted signal reflected from the object is generated by scanning the object with wave energy such as laser beams, microwaves, sonar, or ultrasound.

Another object of the present invention is to provide a system for the remote inspection of structures which is not restricted to small amplitudes and is noise insensitive.

A further object of the present invention is to provide a system for the remote inspection of objects which utilizes a time domain method which permits the real-time imaging of the vibration amplitudes produced by reflection of the object over a region of interest from as little as three samples of quadrature components in the time domain.

A still further object of the present invention is to provide a system for the remote inspection of objects in which a time domain estimator method is utilized but which provides a system which is not restricted to small vibration amplitudes and is not a ratio of harmonic sidebands estimators. Thus, the system is very flexible and noise insensitive.

Briefly described, these and other objects of the invention are accomplished in accordance with its system aspects by using a low frequency vibration source to force the oscillation of an object under investigation and a pulsed ultrasound imaging system is utilized to detect the spatial distribution of vibration amplitude of the object in real-time. Due to the different mechanical properties of the abnormal regions of the object from those of normal regions, vibration patterns of the object at different vibration frequencies are used to determine the abnormalities. A vibration source generates a source of vibrations which is fed to a pulsed or coherent ultrasound imaging device as well as being transmitted onto the object under investigation.

The reflected Doppler shifted waveform generated by reflecting the pulsed ultrasound waves off of the vibrating object under investigation is received by the pulsed ultrasound imaging device which computes the vibration amplitude and frequency of the object in order to form a vibration image. The computations use two alternative methods, either on a frequency domain estimator basis or on a time domain estimator basis. Those methods may or may not include a noise removal process, depending upon the working environment.

The results of calculations of vibration amplitude and phase from some target position are stored in a conventional scan converter which produces an image of the estimates as a function of position over the entire scan plane. Also, synchronization between the estimator systems and the vibration source may or may not be employed, depending upon the actual vibration estimation method utilized.

With these and other objects, advantages and features of the invention that may become hereinafter apparent, the nature of the invention may be more clearly understood by reference to the following detailed description of the invention, the appended claims and to the several drawings attached herein.

DETAILED DESCRIPTION OF THE PREFERRED EMBODIMENT

Figure 1:
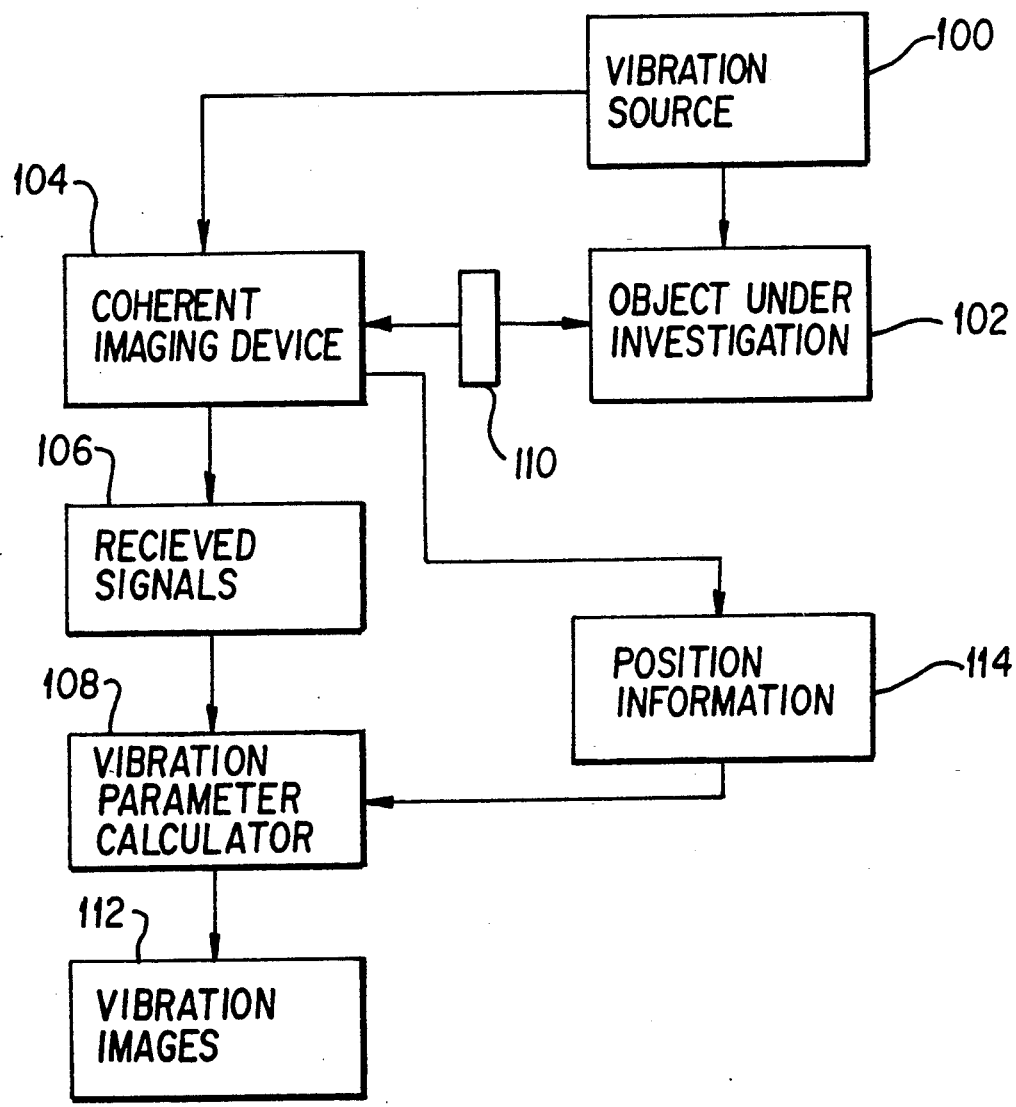
FIG. 1 is a block diagram showing the system of the present invention.

Referring now to detail in the drawings wherein like parts are designated by like reference numerals throughout, there is illustrated in FIG. 1 in block diagram form the overall system of the present invention. A low frequency (approximately 1-1,000 Hertz) vibration source 100 applies a signal to the object under investigation 102 in order to cause the object under investigation 102 to begin vibrating.

An ultrasound transmitter and receiver 110 is used to generate ultrasonic radiation which is aimed at a point on or in the object under investigation. The waves reflected from the object under investigation are received by the receiver portion of the ultrasound transceiver 110 and supplied as an input to the pulse ultrasound imaging device 104. The vibration source 100 is connected to supply the same signal which is used to vibrate the object under investigation 102 to the pulse ultrasound imaging device 104. The pulse ultrasound imaging device 104 may be an ACUSON 128 Color Doppler Imager available from ACUSON, Mountain View, Calif.

The pulse ultrasound imaging device 104 receives the vibration signal generated by the vibration source 100 as well as the ultrasound reflected signals from the object under investigation and utilizes the two signals to produce the received signals 106. The received signals are input into a vibration parameter calculator 108, which may preferably be specialized real-time circuits as shown in FIGS. 3-12. Alternatively, it may be a computer, such as a Sun 3/50 workstation networked to a Sun disk server. Alternatively, a personal computer having real-time digital signal processing characteristics could be utilized in place of the Sun computer.

The vibration parameter calculator 108 generates the vibration images 112 which may be displayed by means of a color or monochrome CRT, laser or other printer or other display device 113.

The pulse ultrasound imaging device 104 is used to detect the spatial distribution of vibration amplitude in real-time. The spatial distribution of the vibration amplitude is generated by means of the vibration source 100, which may preferably be a 5" diameter woofer loudspeaker available from the Radio Shack Division of Tandy Corporation, Dallas, Tex., and others, causing the object under investigation 102 to vibrate, and the ultrasound transceiver 110, which may be a 3.5 MHz or 5 MHz array available from ACUSON.

Due to the different mechanical properties of the abnormal regions of the object under investigation 102 from those of its normal regions, vibration patterns of the object 102 at different vibration frequencies are used to reveal the abnormalities.

It should be understood that the vibration source 100 may use sound or any type of electromagnetic radiation which causes the object under investigation to vibrate. In addition, the ultrasound transmitter and receiver 110 may alternatively utilize any type of coherent, pulsed or continuous electromagnetic radiation that can be detected by the appropriate imaging device 104, for example, light waves, microwaves, etc. It is, however, necessary that both the vibration source 100 and the transmitter 110 utilize coherent radiation which can be readily detected by the imaging device 104.

As disclosed in FIG. 1, the present invention provides for the remote analysis and imaging using, for example, radar, microwaves, sonar, ultrasound, lasers, or any other type of electromagnetic radiation of vibrated structures such as airplanes, bridges, ship hulls or tissue, to detect flaws and cracks as revealed by the abnormal vibration amplitudes generated by such flaws. The stress concentrations which occur around such cracks and flaws are detected by using the Doppler techniques described herein.

The image is generated by scanning the vibrating object under investigation 102 with coherent, pulsed or continuous, focused or unfocussed wave energy such as laser, microwaves, sonar or ultrasound, and analyzing the return signal for Doppler shift properties. By using either the frequency domain estimation method shown and described in connection with FIG. 3 herein or the time domain estimation method shown and described in connection with FIGS. 4-12 herein, the Doppler shifted signal is analyzed 106 to derive the local vibration amplitude of the reflector or object under investigation 102. The result, when combined with information regarding the position of the interrogated object 114 is vibration images 112, which can be displayed as either a gray scale or a color image.

In general, the method of the present invention for the examination of a passive structure requires the application of a swept frequency vibration or audio source, such as the vibration source 100. In examining a passenger aircraft, for example, that may be accomplished by placing a bank of loud speakers in the interior. Vibration sources may also be temporarily mounted on exterior surfaces, such as the wings, hulls of a ship or bridge trusses. The interrogating wave energy generated, for example, by the ultrasound transceiver 110, is then focused on a reference point or within the object. The vibration source 100 is swept over a broad frequency range so as to excite eigenmodes of the object under investigation 102 with relatively high vibrational amplitudes.

Upon finding an appropriate vibration frequency, the interrogating wave energy is scanned over the surface or within a cross-section of the interior of the object under investigation 102 for penetrating waves. The time required for analysis of each spot is less than three cycles of the vibration frequency when the vibration parameter calculator 108 is utilizing the disclosed frequency domain estimator method and a fraction of a single vibration cycle where the vibration parameter calculator 108 is utilizing the time domain estimator method disclosed herein.

The spot size, or spatial resolution of the scan produced by the transceiver 110, depends upon the wavelength used and the particular apparatus. For simply focused coherent sources, it has been found that the spot size will be equal to (1.2)(wavelength)(focal length)/(aperture radius). Since the present invention achieves the use of sub-millimeter wavelengths using ultrasound and optical devices, millimeter scale spatial resolution is achieved. Also, vibrational amplitudes of less than 1/10th of one wavelength of interrogating wave energy can be easily detected utilizing the estimation methods in the vibration parameter calculator 108.

Upon selecting a scan size or region of interest, an image is derived from a point-by-point examination of the Doppler shift in the wave energy reflected by the vibrating object under investigation 102. The image intensity or color is proportional to the vibration amplitude calculated by means of the estimation method which will be described later herein, at each point of the object 102. That image can be inspected for modal shapes as well as abnormally high or low vibration amplitudes, and can also be compared with reference images obtained earlier or from well characterized analogous structures.

Figure 2:
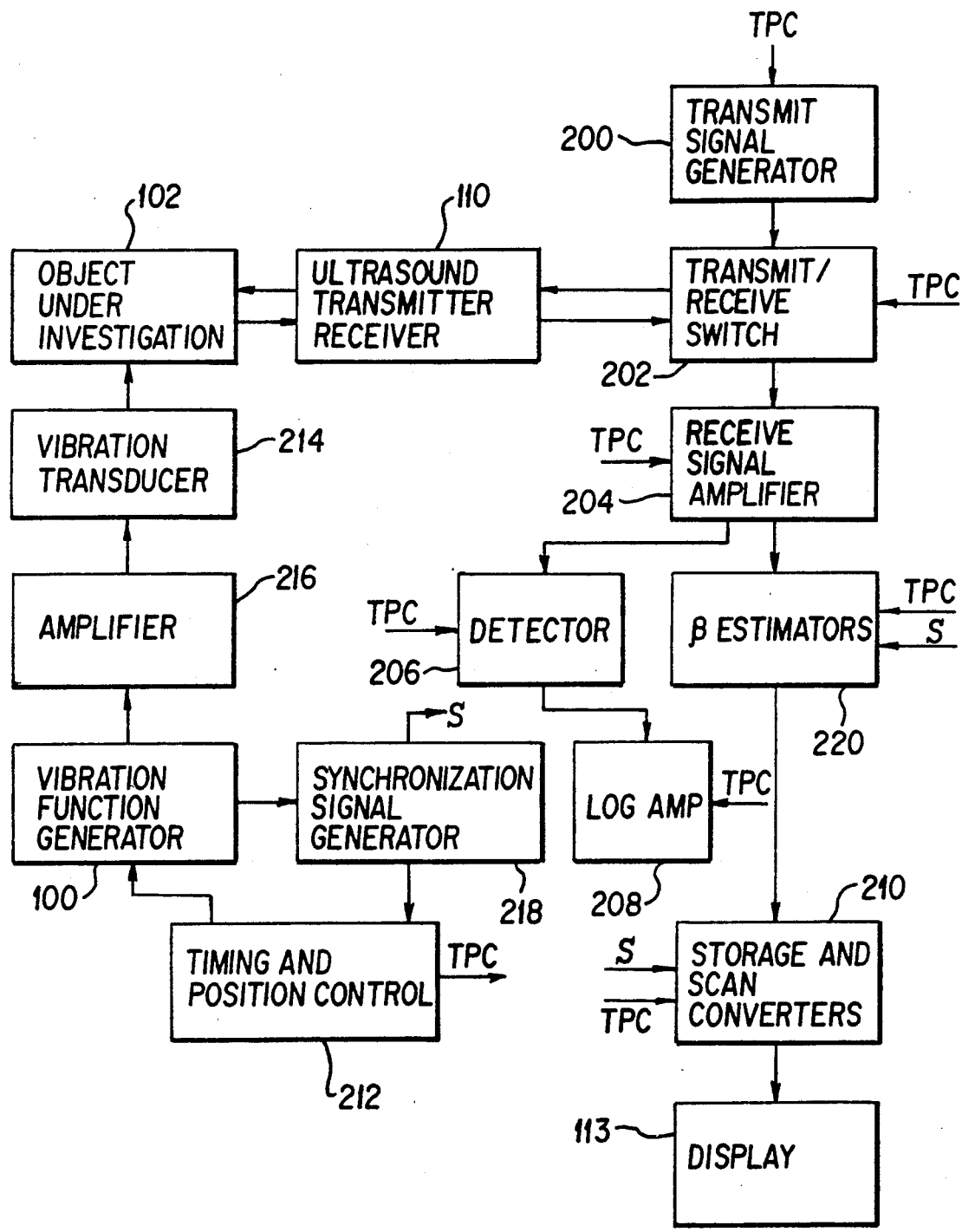
FIG. 2 is a block diagram showing the apparatus of the present invention.

Referring now to FIG. 2, there is shown a block diagram of the apparatus of the present invention. As shown in that figure, the object under investigation 102 is vibrated by a vibration transducer 214 which is powered by an amplifier 216. The amplifier 216 is driven by a vibration function generator or vibration source 100 whose frequency and signal shape are adjustable. After the vibration of the object under investigation 102 has been accomplished, it is scanned by means of an ultrasound transmitter/receiver 110 which is controlled by a transmit signal generator 200 and a transmit/receive switch 202.

The transmitter/receive switch 202 functions to control the mode of operation of the ultrasound transmitter/receiver 110, that is, to place it either in the transmit or receive mode. The transmit/receive switch 202 causes the ultrasound transmitter/receiver 110 to be in the transmit mode while it is receiving a transmit signal from the transmit signal generator 202. If it is not receiving a signal from the transmit signal generator 202, the transmit/receive switch 202 causes the ultrasound transmitter/receiver 110 to be in the receive mode and it functions to transmit the Doppler echo signal received by the ultrasound transmitter/receiver 110 to the received signal amplifier 204.

The output from the received signal amplifier 204 is fed to both a detector 206 and to the beta estimators 220, alternative embodiments of which are shown in more detail in FIGS. 4-12. The output from the detector 206 is fed to a logrithmic amplifier 208 whose output is in turn fed to the storage and scan converter 210. The output from the beta estimators circuitry 220 is likewise fed to the storage and scan converters circuitry 210. The output from the storage and scan converters 210 is the vibration images which are displayed on the display 113.

A timing and position control circuit 212 produces a timing and position control signal which is used to control the vibration function generator 100. A synchronization signal generator 218 receives the output signal from the vibration function generator 100 and generates a synchronization signal S which is fed to both the beta estimator circuitry 220 and the storage and scan converters circuitry 210, as well as the timing and position control circuitry 212. The timing and position control circuitry is also connected to control the transit signal generator 200, the transmit/receive switch 202, the received signal amplifier 204, the detector 206, the logrithmic amp 208, the storage and scan converter circuitry 212 and the beta estimator circuitry 220.

A conventional ultrasound B-scan color Doppler imaging instrument, such as that manufactured by ACUSON described above, includes the equivalent of the transmit signal generator 200, the transmit/receive switch 202, the received signal amplifier 204, the detector 206, the logrithmic amplifier 208, the storage and scan converter circuitry 210, the display 113 and the timing and position control circuitry 212.

Such a conventional ultrasound imaging instrument may be utilized with the following modifications. A vibration transducer 214 is added. A synchronization signal generator 218 generates a synchronization signal based upon the output from the vibration function generator 100 which is fed to the beta estimator circuitry 220 and the storage and scan converter circuitry 210. The synchronization signal consists of information relating to the phase and frequency characteristics of the vibration function generator 100. Those characteristics are used in the calculations performed by the beta estimator circuitry 220 in order to produce the beta estimators. The estimate of beta is stored, together with the conventional ultrasound received signal amplitude in the storage and scan converters circuits 210, which outputs the information collected over the entire scan plane as a video signal of the vibration images to the display 113.

It should be noted that the output from the storage and scan converter circuitry 210 can be two separate images, such as a conventional ultrasound image and a separate image of the variations in beta over the scan plane. Or, the output from the storage and scan converter circuitry 210 may be a signal image with color overlay that can be used to display the beta (vibration) information overlaid on conventional gray scale ultrasound images.

Figure 3:
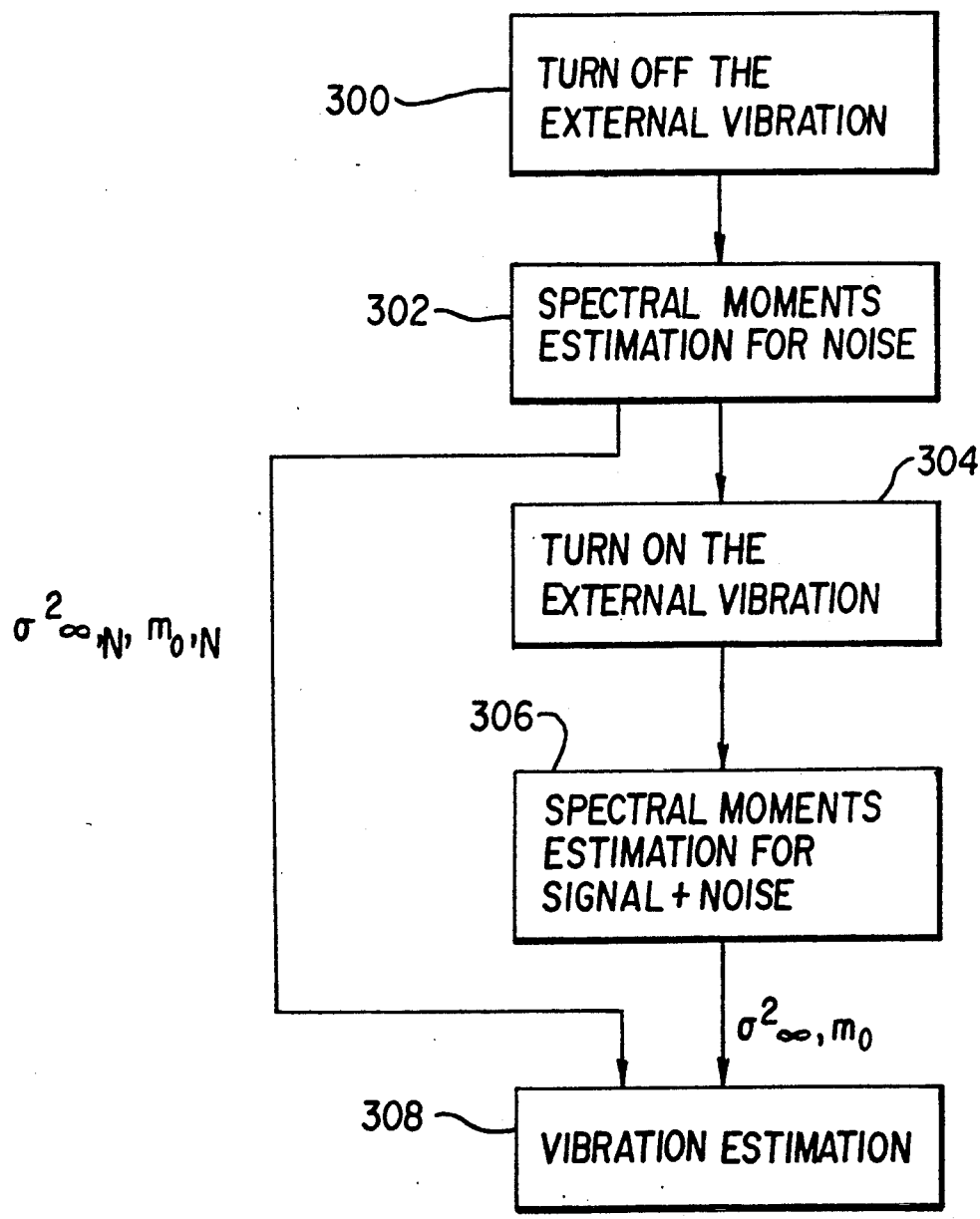
FIG. 3 is a block diagram showing the system for noise correction for the frequency domain estimation method embodiment of the present invention.

FIG. 3 shows the operation of the frequency domain estimation method of the present invention which may be used in conjunction with the vibration parameter calculator 108 or beta estimator circuitry 220 to affect the remote analyzing and imaging of the object under investigation 102. The operation of the frequency domain estimation method is based upon the fact that the Doppler spectrum of echoes of a sinusoidally vibrating scatterer (object under investigation 102) contains discrete spectral lines weighted by Bessel functions of the first kind. The frequency domain estimation method is based upon the use of a new and simple relationship between the spread or variance of the Doppler spectrum of the echoes and the vibration amplitude of the scatterer.

The frequency domain estimation method for use with the remote inspection and analyzing system produces high accuracy even under conditions when the signal-to-noise ratio of the Doppler spectrum return from the scatterer is poor. In addition, deviations caused by slight non-linearities of the vibration of the scatterer have been found to have little contribution to the total estimation error.

Since the scattering object 102 is caused to vibrate slowly by means of the vibration source 100 so as to produce a wavelength much larger than the geometrical dimensions of the scatterer itself, the Doppler spectrum of the signals returning from essentially sinusoidally oscillating structures is similar to that of a pure tone frequency modulation (FM) signal. That spectrum is a Fourier series having spectral lines lying above and below the carrier frequency. The space in between the spectral harmonics is equal to the vibration frequency and the amplitudes of harmonics are given by different orders of Bessel functions of the first kind. Typically, it is desirable to determine the amplitude, phase and frequency of the oscillating structure.

The FM spectrum is well known and, thus, its use in connection with determining a Doppler shift of a moving object will be discussed only briefly. When a moving object is illuminated with an incident laser, radio or acoustic wave, the detected back scattered signals from that moving object contain a frequency shift known as Doppler shift. If the scatterer is oscillating with a vibration velocity much slower than the wave speed and of a vibration frequency much less than the carrier or incident wave frequency, the spectrum of the detected scattered wave will be similar to that of a pure tone FM process since the instantaneous frequency of the scattered waves has a Doppler shift proportional to the vibration velocity. The Doppler spectral moments of the reflected signal are usually defined as:

$$\sigma_\omega^2 = \frac{\int_{-\infty}^{\infty} (\omega - \overline{\omega})^2 S(\omega) d\omega}{\int_{-\infty}^{\infty} S(\omega) d\omega} \tag{1}$$

$$\overline{\omega} = \frac{\int_{-\infty}^{\infty} \omega S(\omega) d\omega}{\int_{-\infty}^{\infty} S(\omega) d\omega} \tag{2}$$

where $\sigma_\omega$ is the Doppler spectral spread and thus $\sigma_\omega^2$ is the variance or second moment, $\overline{\omega}$ is the mean frequency shift of the Doppler spectrum (i.e., the first moment), and $S(\omega)$ is the Doppler power spectrum.

Since the object under investigation 102 is vibrating, the Doppler power spectrum can thus be written as:

$$S(\omega) = \sum_{n=-\infty}^{\infty} J_n^2(\beta) \delta(\omega - n\omega_L) \tag{3}$$

where $W_L$ is the low frequency vibration frequency and where the power spectrum is down shifted to a zero frequency, using, for example, quadrature detection. For this particular Bessel spectrum, the mean frequency $w$ is 0 and the power spectrum is therefore symmetric about a 0 frequency. The zeroth moment only has been noted by Watson in his *Treatise on the Theory of Bessel Functions*, Chapter 2, pp. 14–15, 31, The MacMillan Company, New York, N.Y. (1945) as:

$$1 = \sum_{n=-\infty}^{\infty} J_n^2(\beta) = m_0 \tag{4}$$

The second moment can be derived in a similar way to obtain the result of:

$$\frac{\beta^2}{2} = \sum_{n=-\infty}^{\infty} n^2 J_n^2(\beta) = m_2 \tag{5}$$

In general, all moments of the Bessel spectrum can be calculated from the generating function of the Bessel function given by Watson on page 14, equation (1) of his Treatise. By taking the first through kth derivative of the generating function with respect to z and substituting z=1 into the resulting expressions, all moments of the Bessel spectrum as functions of the parameters can then be calculated from the lower order moments by squaring and simple algebraic manipulation.

Approached from that point of view, the Bessel spectrum becomes a one parameter function. Therefore, the second moment is a good estimator of the spectrum itself. Thus, the vibration amplitude can be estimated from the Doppler spectral spread as:

$$\beta = \sqrt{2} \, \frac{\sigma_\omega}{\omega_L} \tag{6}$$

The above new algorithm indicates that the amplitude parameter beta can be estimated from the standard deviation of the power spectrum.

Even utilizing the above equation, noise still presents a problem in providing a correct parameter estimation. For example, the Doppler signals tend to be 30–50 dB lower than the carrier in many applications. Thus, the signal-to-noise ratio for Doppler signals is usually poor. Therefore, it is necessary to remove stationary and uncorrelated noise from the Doppler spectral spread vibration estimator method result. The signal-to-noise ratio SNR can thus be represented by the $$SNR = \frac{\int_{-\infty}^{\infty} \left( \sum_{n=-\infty}^{\infty} J_n^2(\beta)\delta(\omega - n\omega_L) \right) d\omega}{\int_{-\infty}^{\infty} N(\omega) d\omega} \quad (7)$$

$$= \frac{m_{0,S}}{m_{0,N}} = \frac{1}{m_{0,N}}$$

where $m_{0,N}$ is the zeroth moment of the noise.

As long as the noise is stationary, the moments of the noise power spectrum can be estimated or determined when the vibration is removed or halted. Once the noise moments have been estimated, the noise-free vibrational Doppler spectral spread can then be determined from the noisy signal as:

$$\sigma_{\omega,S}^2 = \sigma_\omega^2 \left( 1 + \frac{1}{SNR} \right) - \frac{1}{SNR} \sigma_{\omega,N}^2 \quad (8)$$

Even in some applications in which the vibration is inherent and cannot be controlled externally, the noise compensation can be performed by estimating the signal-to-noise ratio as well as the Doppler spectral spread of the noise from the finite band with white noise. Even if the noise is not white, the noise compensation can still be provided as long as the noise power and noise spectral spread can be estimated by statistical techniques.

The method for applying the frequency domain estimation system is shown in FIG. 3. First, the external vibration source 100 is turned off at step 300. Then, the spectral moments estimation for noise is performed at step 302. This is done using conventional methods such as taking the Fourier transform of the noise and deriving the appropriate integrals from the transform, or by taking the appropriately weighted derivative of the time domain auto-correlation function. The result of the spectral moments estimation for noise at step 302 is the signals representing the variance or second moment of the Doppler spectral spread, $\sigma_{\omega,N}^2$, and the zero moment of the noise, $M_{0,N}$. Both of those two signals are fed to step 308.

After the spectral moments estimation for the noise in the Doppler spectral spread has been completed at step 302, the external vibration source is turned on at step 304 and then the spectral moments estimation for the signal plus noise is produced at step 306 by conventional techniques. The result of the spectral moments estimation for the signal plus the noise at step 306 is the variance of the Doppler spectral spread $\sigma_\omega^2$ and the zeroth moment of the Doppler spectral spread $M_O$. Both of those signals are fed to the vibration estimation step 308 which utilizes equation (8) to produce the vibration estimation of the amplitude which is output by the vibration parameter calculator 108.

As readily apparent to those of ordinary skill in the art, each of the steps 300, 302, 304, 306 and 308 shown in FIG. 3 can be implemented by means of a computer such as vibration parameter calculator 108, which, in addition to controlling the operation of the vibration source 100, functions to calculate the spectral moments for both the noise and signal plus noise Doppler spectra, as well as utilizing the results of those calculations to produce the vibration estimation result and thus the vibration images 112.

Figure 4:
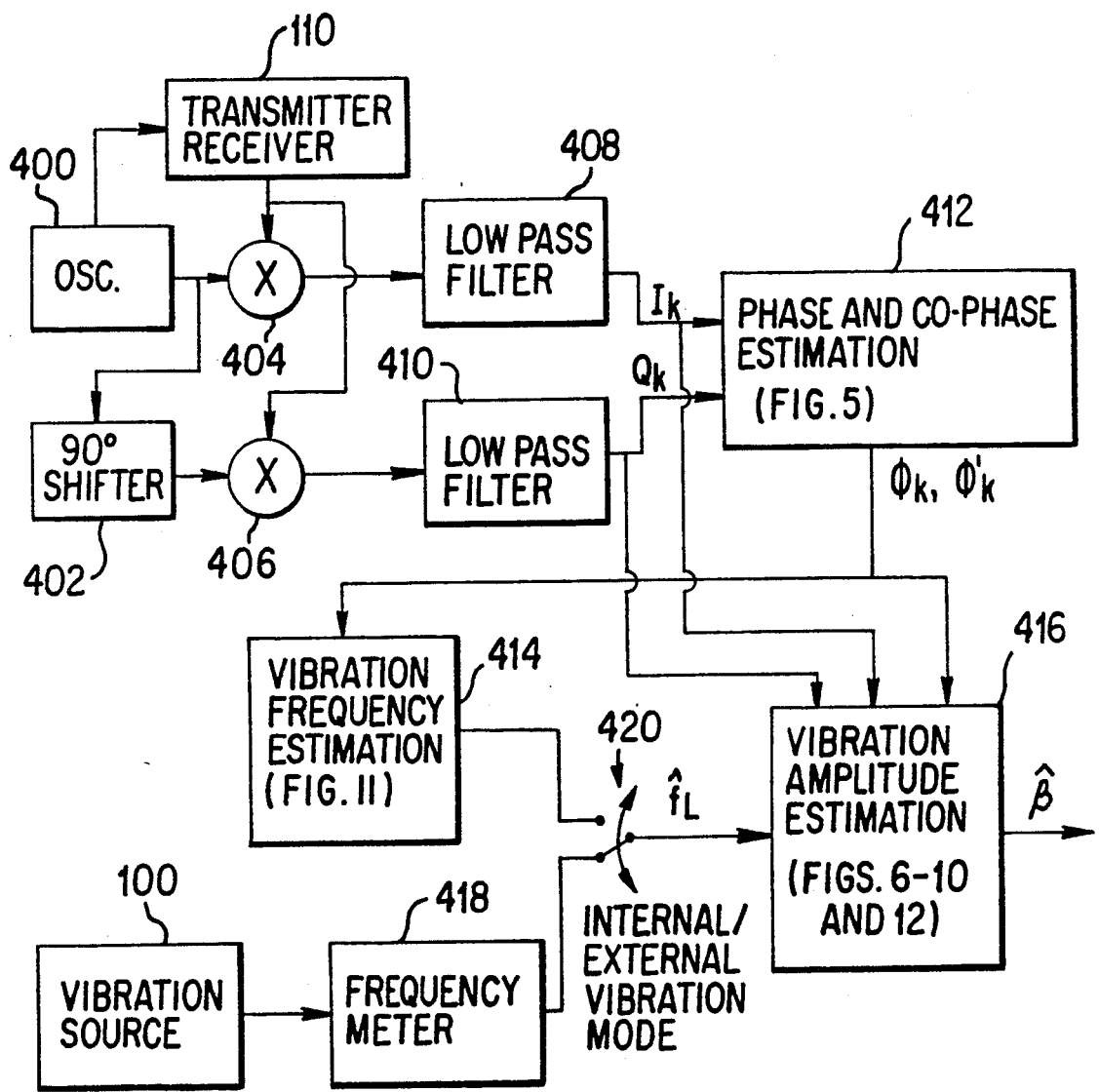
FIG. 4 is a block diagram showing the system for the time domain estimation method embodiment of the present invention.

FIG. 4 shows a schematic block diagram of the time domain estimation system which may be used in connection with the vibration source 100, the ultrasound transmitter/receiver 110 and vibration parameter calculator 108 of FIG. 1 to perform non-destructive testing, sonoelasticity imaging or other remote monitoring and analysis of structures and soft tissue, as previously described. That is accomplished by estimating the amplitude and frequency of a relatively low frequency vibration of a target which has been interrogated with a relatively high frequency wave.

The method and system shown in FIG. 4 is based upon the Doppler shift generated by the vibrating target, which produces a frequency modulated echo signal. The system of FIG. 4 uses only a small fraction of the low frequency vibration cycle of the object under investigation 102 to obtain the estimated parameters. Therefore, real-time imaging of the vibration of the object under investigation 102 can readily be made.

The system of FIG. 4 includes methods which complement each other to cover a wide variety of the estimated parameters and different sampling, scanning and imaging criteria which are confronted in practice. The methodology implemented in FIG. 4 produces good noise performance and low sensitivity to non-linearities of the vibration which may be present in non-ideal conditions of operation.

Although the pulsed Doppler technique has been successfully applied for blood flow detection for over 15 years, all of the research towards utilizing Doppler spectral parameter estimations involving time and frequency domain processing have been oriented towards steady and slowly varying or pulsatile blood flow. Such estimations are not suitable for the applications of vibration amplitude detection using Doppler ultrasound.

Vibration images are also desirable for use in sonoelasticity imaging for detecting a hard tumor surrounded by relatively soft tissues. The principle of sonoelasticity imaging involves the vibration of the tissue by an external source which generates a "low" frequency compared to the investigating wave, such as the vibration source 100. Regions of abnormal elasticity produce abnormal vibration amplitudes.

Since the Doppler spectrum received from a vibrating target is symmetric about the center frequency, the mean frequency is zero. Therefore, conventional time domain and frequency domain velocity and "turbulence" estimators are not appropriate for detecting vibration such as that disclosed in U.S. Pat. No. 4,853,904, to Pesque, and thus estimators based upon time domain processing must be used for sonoelasticity imaging and other applications where varying types of propagating waves, for example, ultrasound, laser, microwave and radio wave, are utilized to detect oscillating structures. See also "Real-Time Two-Dimensional Doppler Flow Mapping Using Auto-Correlation", *Acoustical Imaging*, M. Kaveh et al., ed., Volume 13, Plenum Press, pp. 447–460 (1984).

The estimating methods disclosed herein utilize only very few samples of the Doppler signal and the resulting estimation has only a weak connection with the phase of low frequency vibration. Thus, the present invention achieves an asynchronous real-time two-dimensional "sonoelasticity imaging" or vibration imaging system which overcomes the shortcomings of the prior art.

The problem of estimating the vibrational parameter underlies several other applications aside from that of "sonoelasticity imaging". For example, other areas of application include remote sensing, radar, sonar, acoustics and laser calibration of sound fields. In the past, since the time domain waveform is complicated, frequency domain techniques were the primary object of efforts to analyze the vibrational parameters. A new and simple solution to the use of frequency domain methods has been discussed in connection with FIG. 3.

Since known techniques typically require a long sequence of Doppler signal to be analyzed in order to avoid frequency aliasing and to achieve noise reduction in extracting low-magnitude spectral components, they are not well suited to making real-time images. However, the time domain processing system of the present invention requires less data than frequency domain approaches, including that disclosed herein, to achieve the same estimation and is therefore more suitable for real-time and/or imaging applications.

For the simplified case of a sinusoidally vibrating target, the Doppler returned signal can be represented by a pure tone frequency modulation (FM) process such that the receipt signal can be written as $$S_r(t) = A \cos(\omega_0 t + \beta \sin(\omega_L t + \phi)) \quad (10)$$

"'Sonoelasticity' images derived from ultrasound signals in mechanically vibrated tissues", R. M. Lerner, S. R. Huang, Kevin J. Parker, *Ultrasound in Medicine & Biology*, Vol. 16, No. 3, pp. 231–239, 1990. Since the modulation index of the FM process, beta, is directly related to the vibrational amplitude of the velocity or displacement field, beta is equal to $$\beta = \frac{2v_m \omega_0 \cos\theta}{\omega_L c_0} \quad (11)$$

$$= \frac{2\xi_m \omega_0 \cos\theta}{c_0}$$

$$= 4\pi \cos\theta \left(\frac{\xi_m}{\lambda_0}\right)$$

where $\lambda_0$ is the vibration amplitude of the displacement field, $\omega_0$ is the wavelength and theta is the angle between the wave propagation and the vibration vectors. Thus, the estimation of the modulation index, beta, is equivalent to the estimation of the vibration amplitude of the displacement and/or velocity fields.

If a synchronous detection is used to detect the Doppler signal, then the resulting two discrete quadrature signals can be represented as:

$$I_k = \cos(\beta \sin(k\omega_L T_s + \Phi)) \quad (12)$$

$$Q_k = \sin(\beta \sin(k\omega_L T_s + \Phi)) \quad (13)$$

where $T_3$ is the sampling period, and k is the sample number: 1, 1, 3 ...

Since the cross products of two quadrature sinusoidal signals can be simplified using trigonometric identities, those two signals can be defined as:

$$\phi_k = \tan^{-1}\left(\frac{I_k Q_{k-1} - I_{k-1} Q_k}{I_k I_{k-1} + Q_k Q_{k-1}}\right) \quad (14)$$

$$= -[\beta \sin(k\omega_L T_s + \Phi) - \beta \sin((k-1)\omega_L T_s + \Phi)]$$

$$= -2\beta \cos\left(k\omega_L T_s - \frac{\omega_L T_s}{2} + \Phi\right)\sin\left(\frac{\omega_L T_s}{2}\right)$$

$$\phi'_k = \tan^{-1}\left(\frac{I_k Q_{k-1} + I_{k-1} Q_k}{I_k I_{k-1} - Q_k Q_{k-1}}\right) \quad (15)$$

$$= -[\beta \sin(k\omega_L T_s + \Phi) + \beta \sin((k-1)\omega_L T_s + \Phi)]$$

$$= -2\beta \sin\left(k\omega_L T_s - \frac{\omega_L T_s}{2} + \Phi\right)\cos\left(\frac{\omega_L T_s}{2}\right)$$

Those two signals are referred to as "phase" and "co-phase" signals and are both related to the phase of the received signal. Derivations of those two signals involve the complex multiplications of two successive complex quadrature signals. Upon examining those two signals closely, it is seen that they are 90° out-of-phase with different amplitude multipliers. In other words, they are the phase-shifted and amplified versions of the vibration signals.

Therefore, to estimate the vibration amplitude, it is known that the sum and the difference of successive samples of the phase signal can be written in the forms $$\phi_k^- \equiv \phi_k - \phi_{k-1} \quad (16)$$

$$= -4\beta \sin(k\omega_L T_s + \Phi)\sin\left(\frac{\omega_L T_s}{2}\right)\sin\left(\frac{\omega_L T_s}{2}\right)$$

and $$\phi_k^+ \equiv \phi_k + \phi_{k-1} \quad (17)$$

$$= -4\beta \cos(k\omega_L T_s + \Phi)\cos\left(\frac{\omega_L T_s}{2}\right)\sin\left(\frac{\omega_L T_s}{2}\right)$$

Thus, if the vibration frequency is known, the vibration amplitude can be estimated directly from the above equations as:

$$\beta_1 = \quad (18)$$

$$\sqrt{\frac{\left\{\phi_k^- \cos\left(\frac{\omega_L T_s}{2}\right)\right\}^2 + \left\{\phi_k^+ \sin\left(\frac{\omega_L T_s}{2}\right)\right\}^2}{4\sin^2(\omega_L T_s)\sin^2\left(\frac{\omega_L T_s}{2}\right)}}$$

The above estimator is referred to as the "successive-phase estimator". Since the sum and difference of successive "phase" and "co-phase" signals are essentially the same, the same estimation can be obtained using the sum and difference of the two successive samples of co-phase signals. If both the phase and co-phase signals are available, the estimation can be achieved by combining those two signals. Since both phase and co-phase signals have contributions depending upon the sampling rate, this estimator is called the "bi-phase estimator". It requires an additional arc tangent operation than does the successive-phase estimator; however, it is less sensitive to the variation of the sampling rate.

Noise is reduced during the instant estimation process by the cross multiplications of in-phase and quadrature-phase signals ($I_k$ and $Q_k$) in order to derive the phase and co-phase signals as shown in equations (12) and (13). By applying the same technique, the cross products of the phase and co-phase signals can be used to achieve additional noise reduction in the following form:

$$\bar{\beta}_3 = \sqrt{\frac{(\phi_k \phi'_{k-1} - \phi_{k-1}\phi'_k)}{2\sin^2(\omega_L T_s)}} \tag{19}$$

That equation is referred to as the the 1-shift cross-phase estimator which can easily be generalized to n-shifts for flexible signal processing.

In all of the foregoing estimations, the vibration frequency of the vibration source 100 must be known before the vibration amplitude can be estimated. In some applications, the vibration of the object under investigation 102 is externally forced, such as shown in FIG. 1, and the vibration frequency can then be accurately and precisely tracked using a frequency meter 18 as shown in FIG. 4. Such is the case when conducting sonoelasticity imaging and laser calibration and measurement of sound fields. In other applications, in which internal vibrations apply, for example, heart valve vibration, the frequency of vibration is unknown and that important parameter needs to be estimated.

By taking the ratio of the difference of the phase and the sum of the co-phase signals, the "phase-ratio estimator" or vibration frequency can be shown to be:

$$\bar{f}_L = \frac{\tan^{-1}\left(\sqrt{\frac{\phi_k - \phi_{k-1}}{\phi_k + \phi_{k-1}}}\right)}{\pi T_s} \tag{20}$$

All of the algorithms discussed above use a fixed number of samples to estimate the parameters. Thus, the only way in which noise performance can be improved is by averaging the number of samples over the estimated parameters. However, the noise may be amplified in the process of performing those calculations, therefore, the performance improvement is somewhat limited. Since, for a small modulation index, noise causes more serious problems in estimations, another estimation method which performs an averaging operation over the raw data has been developed.

It is well known that the spectrum of the pure tone FM signal is a series of Bessel functions. If $x(t)$ represents the complex quadrature signal, $$\chi(t) = \cos(\beta\sin(\omega_L t + \phi)) + i\sin(\beta\sin(\omega_L t + \phi)) \tag{21}$$

the desired vibration amplitude can be estimated as $$\bar{\beta}_4 = \sqrt{\frac{1 - R_{xx}(T_s)}{\sin^2\left(\frac{\omega_L T_s}{2}\right)}} \tag{22}$$

when the estimated parameter beta is small. This is referred to as the "auto-correlation estimator" for vibration amplitude.

In practice, the auto-correlation function is approximated by a finite series:

$$R_{xx}(K, T_s) \approx \frac{1}{N}\sum_{n=0}^{N-1} X_{k-n}X^*_{k-n-1} \tag{23}$$

where $x_k$ is the discrete complex quadrature signal $I_k + iQ_k$. The parameter N can be varied according to real conditions, for example, the sampling rate, noise level and synchronization. The longer the sequence is used to approximate the auto-correlation, the better the estimate becomes. In practice, four to ten samples can be used to produce a good approximation.

If the RF sampling rate is sufficiently high, the vibration estimation can be achieved as has been previously described. In the case which the sampling frequency is not sufficiently high or the only real RF signal (either sine or cosine or a phase-shifted sine component) is available, the vibration can still be estimated after correction of the sine and/or cosine factors and the auto-correlation can be expressed as:

$$R(\sigma) - \frac{1}{2}(2\beta^2)\cos(W_o\pi)$$

This equivalence of signal processing in both the base-band and RF domains provides a high degree of freedom and flexibility in the design of system architecture, electronic circuitry and signal processing.

The vibration amplitude can also be estimated using conventional Doppler estimators. Since the modulated signal is sinusoidally vibrating, the output of a conventional mean Doppler frequency estimator is also a sinusoidal function. The frequency of this sinusoid is the vibration frequency and the amplitude is proportional to the modulation index or vibration amplitude. Therefore, one can also upgrade a conventional Doppler estimator with some modifications.

But, due to the nature of a truncated sequence used in conventional Doppler estimators, large bias or variance of the resulting estimates of the sinusoidal amplitude are often encountered. Thus, to reduce the bias and variance, the estimation time can be made longer than that of the estimation techniques discussed above. Nonetheless, it is still worthwhile discussing some approaches to modify a conventional Doppler into vibration Doppler estimates.

The first way to find the amplitude of the sinusoid is to differentiate or to integrate the sinusoidally vibrated estimate. Let the conventional mean Doppler frequency estimate be $$y(t) = \beta\sin(W_L t + \Phi). \tag{27}$$

Therefore, the vibration amplitude can be estimated as:

$$\beta = \left[y^2(t) + \frac{1}{\omega_L^2}\left(\frac{dy(t)}{dt}\right)^2\right]^{\frac{1}{2}} \tag{28}$$

or $$\beta = [y^2(t) + \omega_L^2 (\int y(t)dt)^2]^{\frac{1}{2}}$$

That method is very general but the performance depends on how well the time derivative or integration can be achieved. The time derivative and integration can be either derived from the conventional Doppler estimate or directly derived from the RF signal. For direct RF estimation, that translates to the use of displacement, velocity, and/or acceleration estimators. For example, since the time shift of the RF correlation peak between pulses is proportional to the displacement, and velocity can be derived from the amount of time shift of the RF correlation peak in a few successive pulses, (as per U.S. Pat. No. 4,853,904, to Pesque), those two signals can be combined to estimate the vibration amplitude.

Another approach is to use spectral estimation techniques to estimate the power or amplitude of a truncated sinusoid. Among those spectral estimation techniques, the AR (autoregressive) and ARMA (autoregressive and moving average) models suffer from the stochastic nature of the modeling and therefore the resulting estimates are oscillating as a function of truncation length, initial phase of the sampled sinusoid, sampling frequency, etc. Therefore, the sampling must be held at a certain fixed operating point and the vibration frequency cannot be changed or swept during the estimation. That restricts the use of the vibration and the scanning. Some other methods employ sinusoidal models and might perform better. Examples are Pisarenko Harmonic Decomposition and Prony Spectral Line Estimation, as discussed in "Spectrum analysis—a modern perspective", S. M. Kay and J. S. Marple, Proc. IEEE Vol. 69, pp. 1380–1419, November 1981. For all spectral estimation techniques, the major disadvantage is the intensive computation involved in the least square minimization.

Figure 13A:
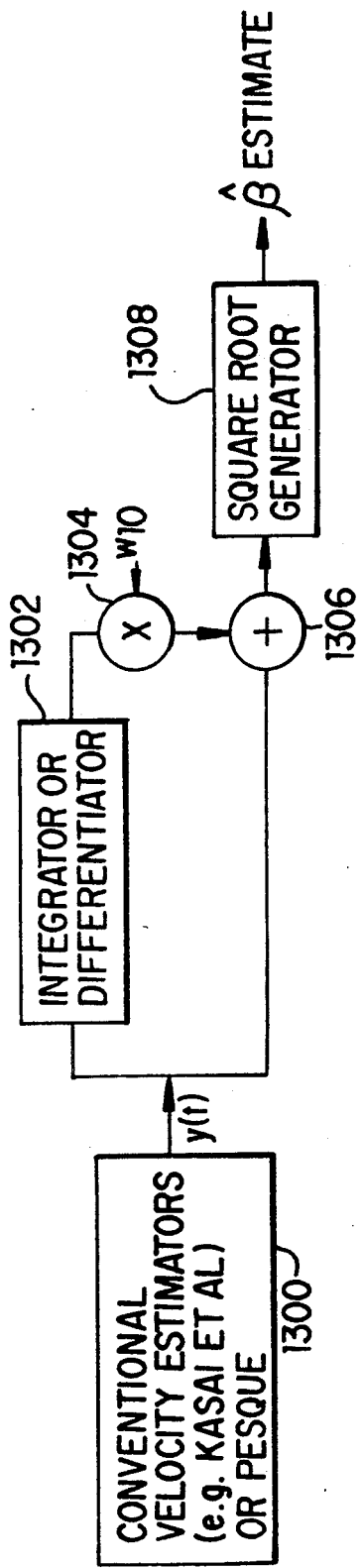
FIG. 13A is a schematic block diagram illustrating how a conventional velocity estimator can be utilized to provide an improved approximate estimation of vibration amplitude signal.
Figure 13B:
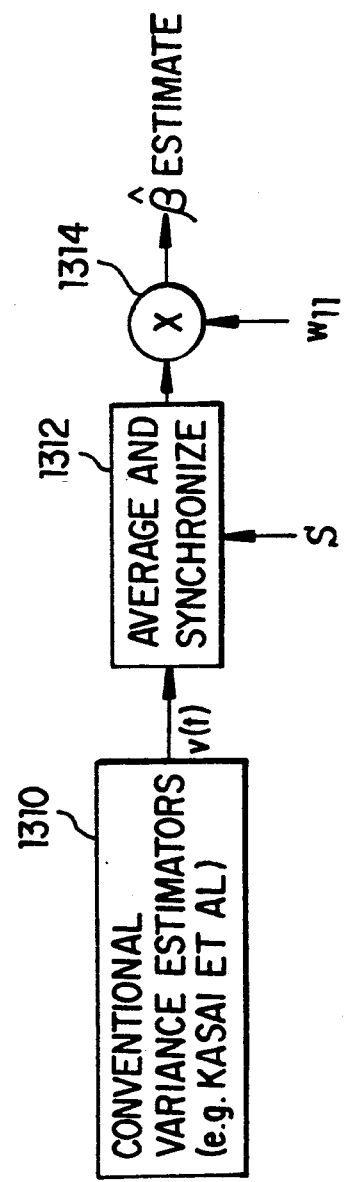
FIG. 13B is a schematic block diagram showing how a conventional variance estimator can be utilized to produce an improved approximate estimation of vibration amplitude signal.

Another way to adapt conventional Doppler techniques is to utilize the new discovery by the present inventors that the vibration amplitude is proportional to the spectral variance of the Doppler signal. Some conventional methods for estimating "turbulence" or variance have been applied to blood flow. C. Kasai et al., "Real-Time Two-Dimensional Blood Flow Imaging Using an Autocorrelation Technique", IEEE Trans. Sonics Ultrason., Vol. Su-32, pp. 458–463, May 1985. In the presence of a vibrating target, these estimates would oscillate, but could be adapted with synchronization to the vibration source, as well as by averaging techniques. An example of the application of the teachings of the instant invention to improving the conventional methods of estimating are shown in FIGS. 13a and 13b which are discussed later herein.

FIG. 4 shows the time domain processing system embodiment for use with the present invention. As shown in that figure, an oscillator 400 is used to control the frequency of oscillation of the transmitter/receiver 110. The output from the transmitter/receiver 110 is fed to a first multiplier 404 which also receives the output signal from the oscillator 400. The oscillator 400 also applies its output signal to a 90° shifter 402, which shifts the phase of the output from the oscillator 400 by 90° and then applies it to a second multiplier 406. As shown in FIG. 4, the output from the transmitter/receiver 110 is also applied to the second multiplier 406.

The output from each of the respective multipliers 04 and 406 is fed to respective low pass filters 408 and 10 which function to eliminate the unwanted double frequency signals. The output from the low pass filter 408 is the first quadrature signal $I_k$. The output from the second low pass filter 410 is the second quadrature signal $Q_k$. The outputs from both of the low pass filters 408, 410 are provided to the input of the phase and co-phase estimation block 412.

Figure 11:
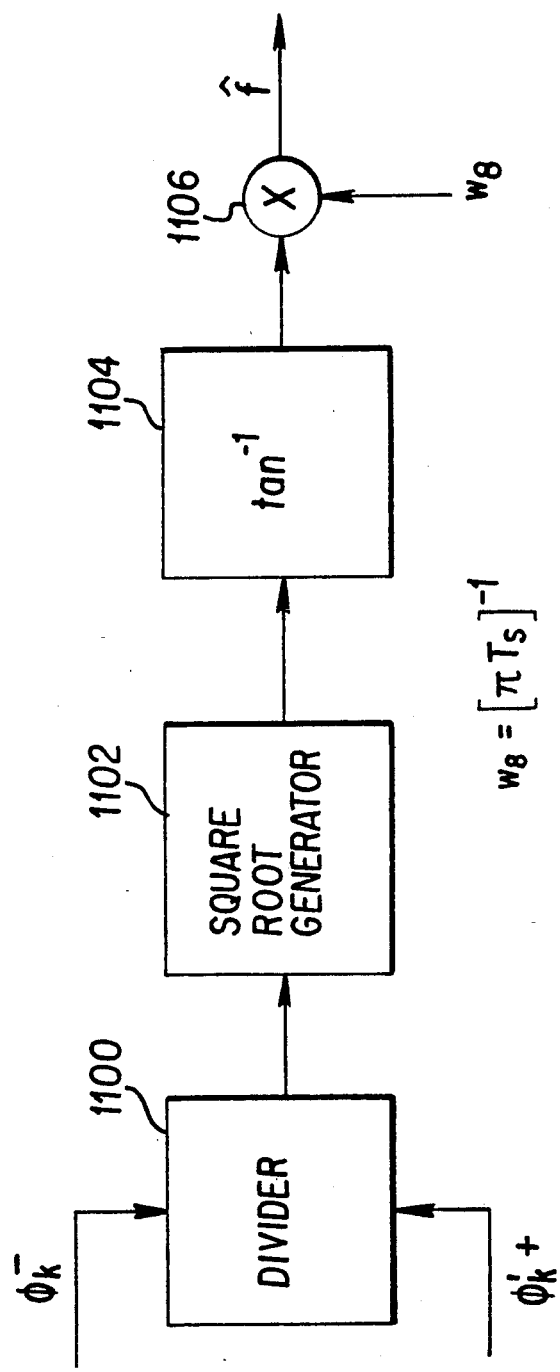
FIG. 11 is schematic block diagram of the phase-ratio estimator circuitry for vibration frequency estimation for use as part of the circuitry of FIG. 4.

The output from the phase and co-phase estimation block 412 is fed to the input of the vibration frequency estimation block 414, whose circuitry is shown in FIG. 11. It is also fed to the input of the vibration amplitude estimation block 416 which, in conjunction with the vibration parameter calculator 108, functions to produce the desired vibration amplitude signal beta.

The vibration amplitude estimation block 416 also receives as an input the output signals from the low pass filters 408, 410 and a vibration frequency signal, which will be described later. The vibration amplitude estimation block 416 solves equation numbers 6, 8, 18, 19, 22 and 24 and in order to produce the desired vibration amplitude estimation.

When the system of the present invention is operated in an external vibration mode, the output from the vibration source 100, in addition to being provided to the pulse ultrasound imaging device 104 and being used to vibrate the object under investigation 102, it is fed to a frequency meter 418 which produces a signal representative of the vibration frequency. When switch 420 is in the external vibration mode setting, as is shown in FIG. 4, that frequency signal is provided as the fourth input to the vibration amplitude estimation block 416. When the switch 420 is in the internal vibration mode, the output from the vibration frequency estimation block 414 is provided as the frequency signal to the vibration amplitude estimation block 416.

FIGS. 5–10 show the various circuitry which may be utilized either singly, or in combination with the circuitry shown in those figures, for providing the phase and co-phase estimations.

Figure 5:
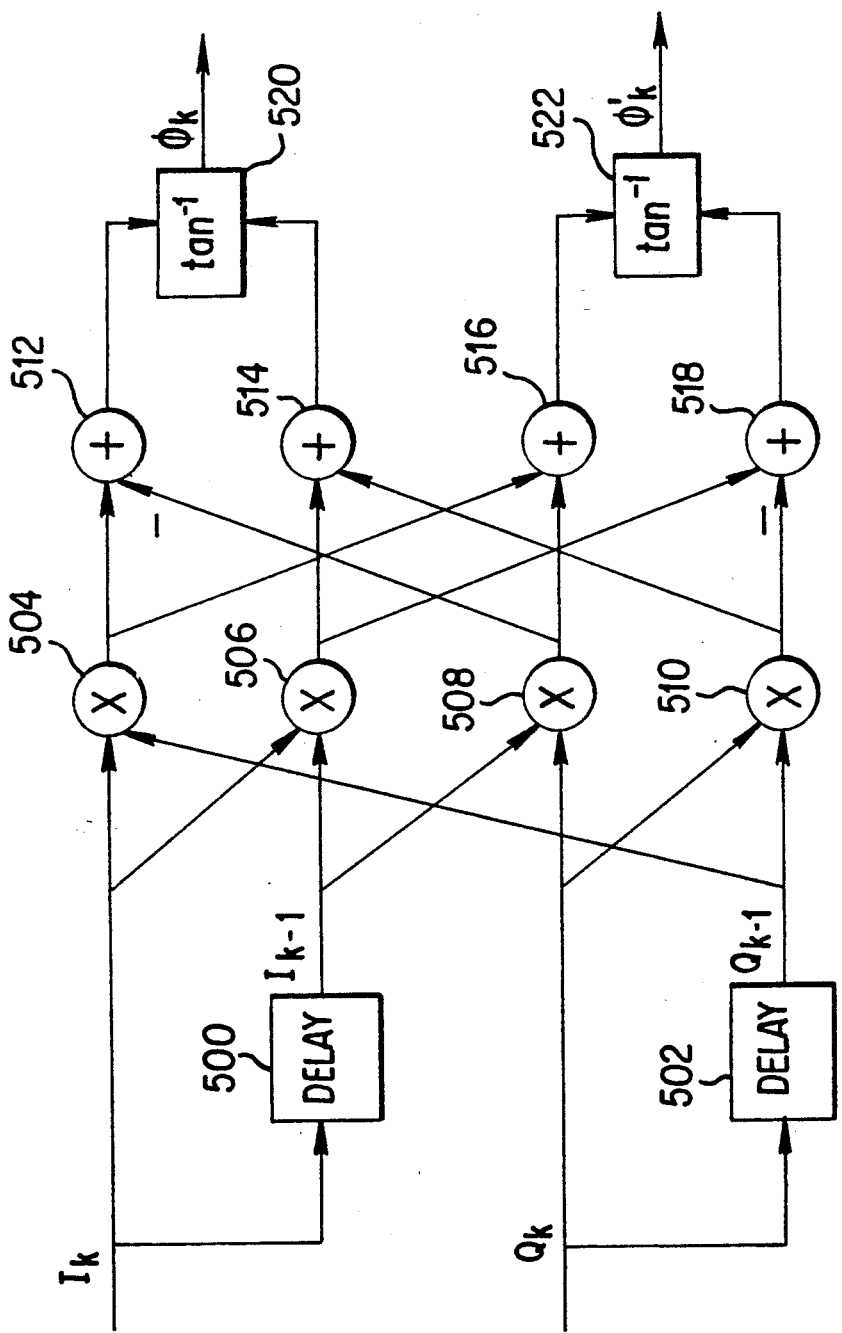
FIG. 5 is a schematic block diagram showing the phase and co-phase signal estimation system for the time domain estimation system of FIG. 4.
Figure 6:
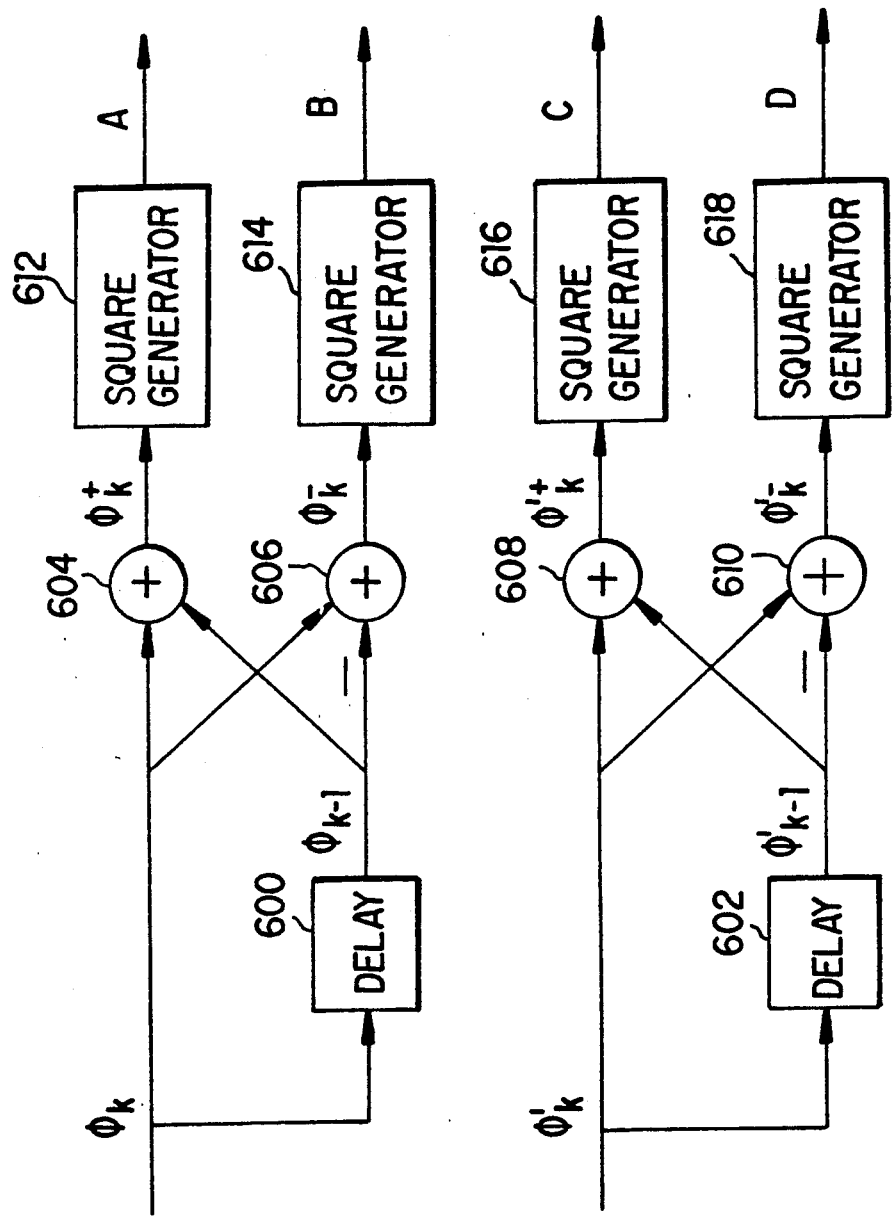
FIG. 6 is schematic block diagram of additional phase processing circuitry which may be utilized in connection with the time domain processing circuitry of FIG. 4.

In FIG. 5, $I_k$ and $Q_k$, the quadrature components, are input and the circuit computes the phase and co-phase parameters $\phi_k$, $\phi'_k$. In FIG. 6, the phase and co-phase signals are combined with delayed versions of those signals to form the intermediate parameters A, B, C & D.

Figure 7:
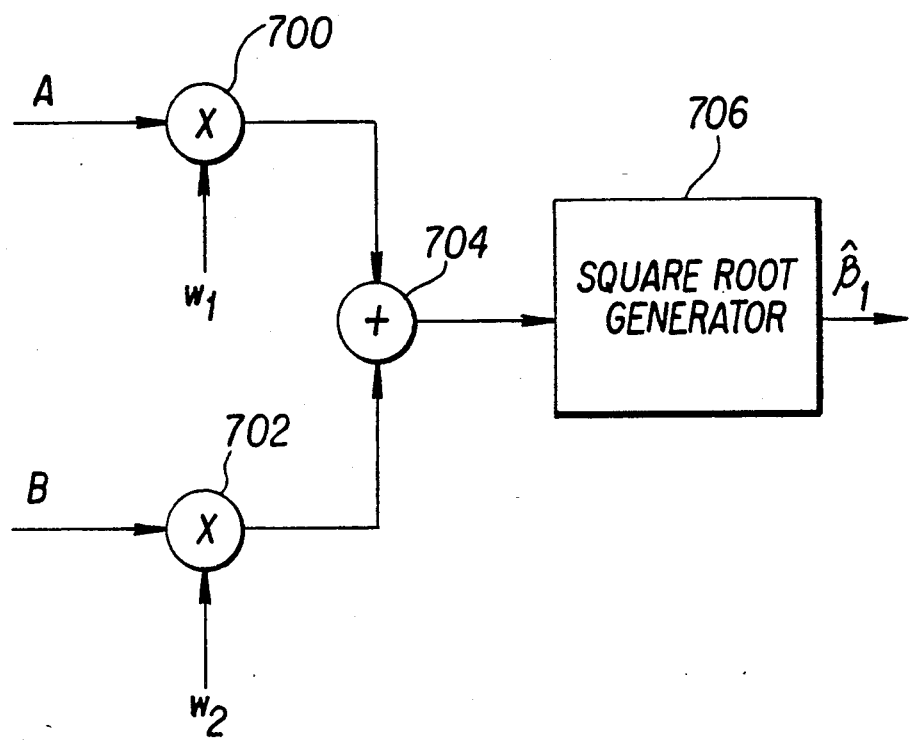
FIG. 7 is a schematic block diagram of successive-phase estimator circuitry which may be utilized in connection with the phase and co-phase estimation circuitry of FIG. 4.

FIG. 7 shows the use of the intermediate parameters A & B, combined with the scale factors $W_1$ and $W_2$, to form the successive phase estimate.

Figure 8:
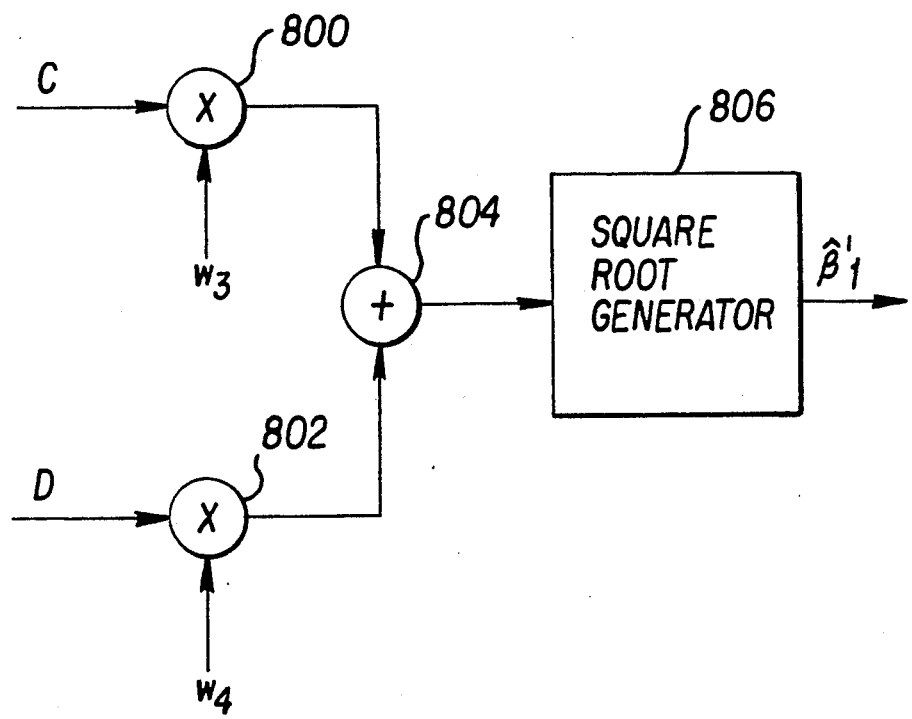
FIG. 8 is a schematic block diagram of successive co-phase estimator circuitry which may be utilized in connection with the phase and co-phase estimation circuitry of FIG. 4.

FIG. 8 shows the use of the intermediate parameters C and D, together with the scale factors, $W_3$ and $W_4$, to product the successive co-phase estimate.

Figure 9:
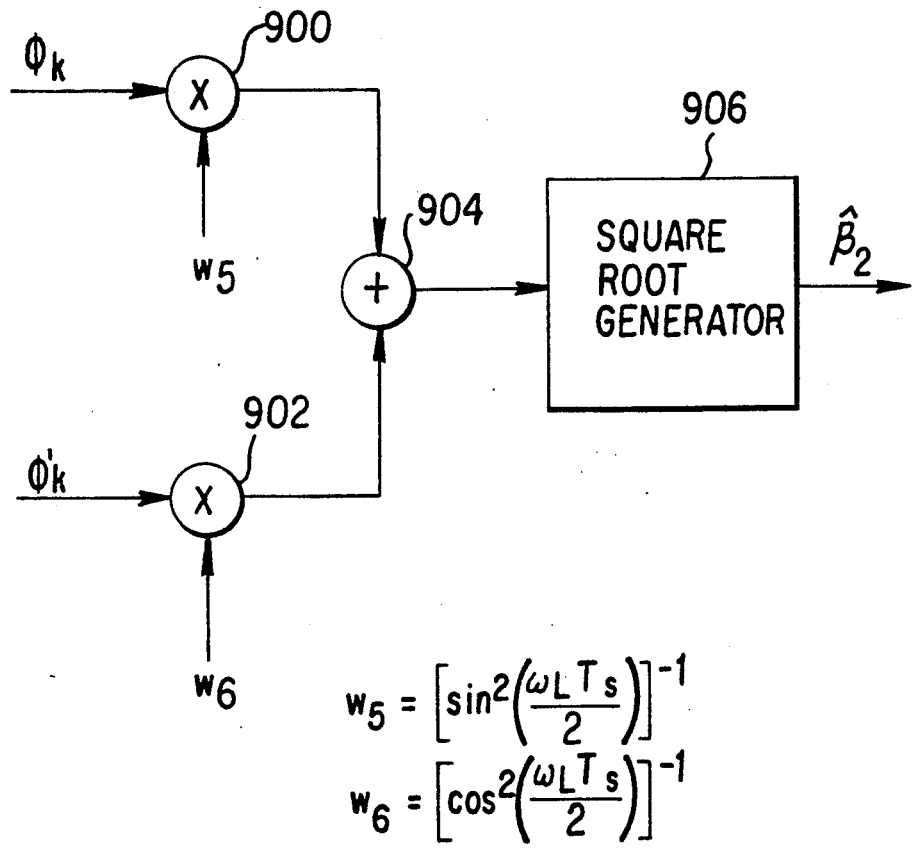
FIG. 9 is a schematic block diagram of bi-phase estimator circuitry which may be utilized with the phase and co-phase estimation circuitry of FIG. 4.

FIG. 9 shows the use of the phase and co-phase signals, combined with the scale factors $W_5$ and $W_6$, to produce the bi-phase estimate.

Figure 10:
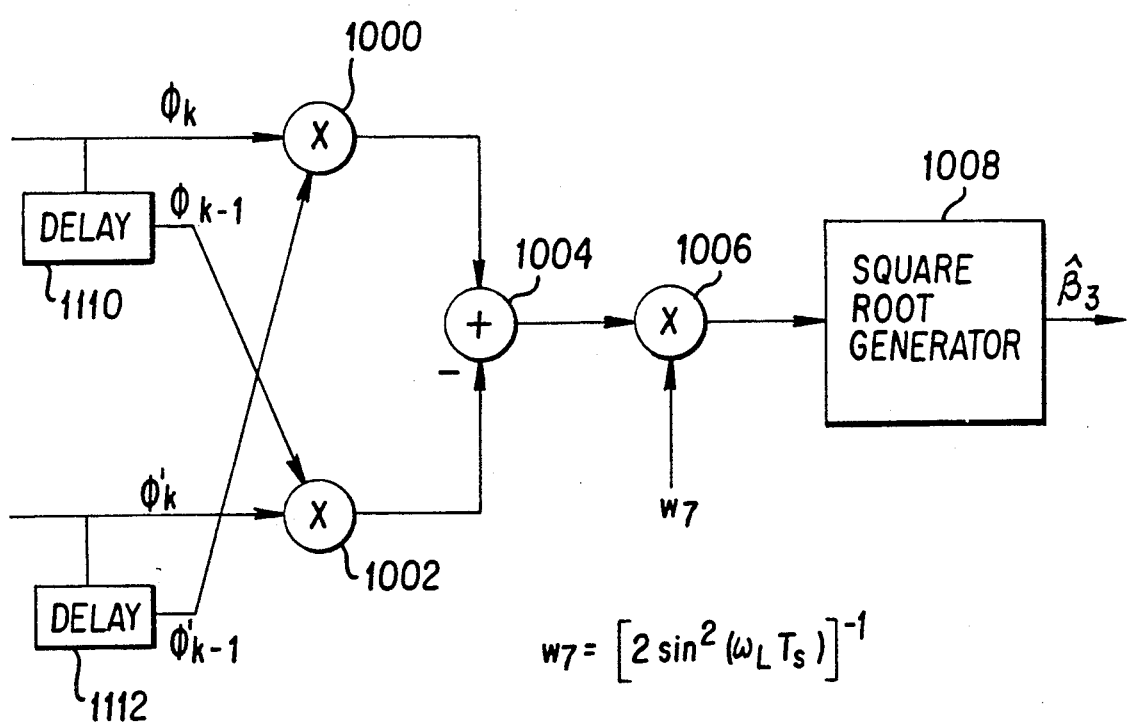
FIG. 10 is schematic block diagram of 1-shift cross-phase estimator circuitry which may be utilized with the phase and co-phase estimation circuitry of FIG. 4.

FIG. 10 shows the combination of the phase and co-phase and delayed versions combined with the scale factor $W_7$, to produce the 1 shift estimator.

FIG. 11 shows the combination of the phase difference and co-phase difference signals, together with the scale factor $W_8$, to produce the vibration frequency estimate.

Figure 12:
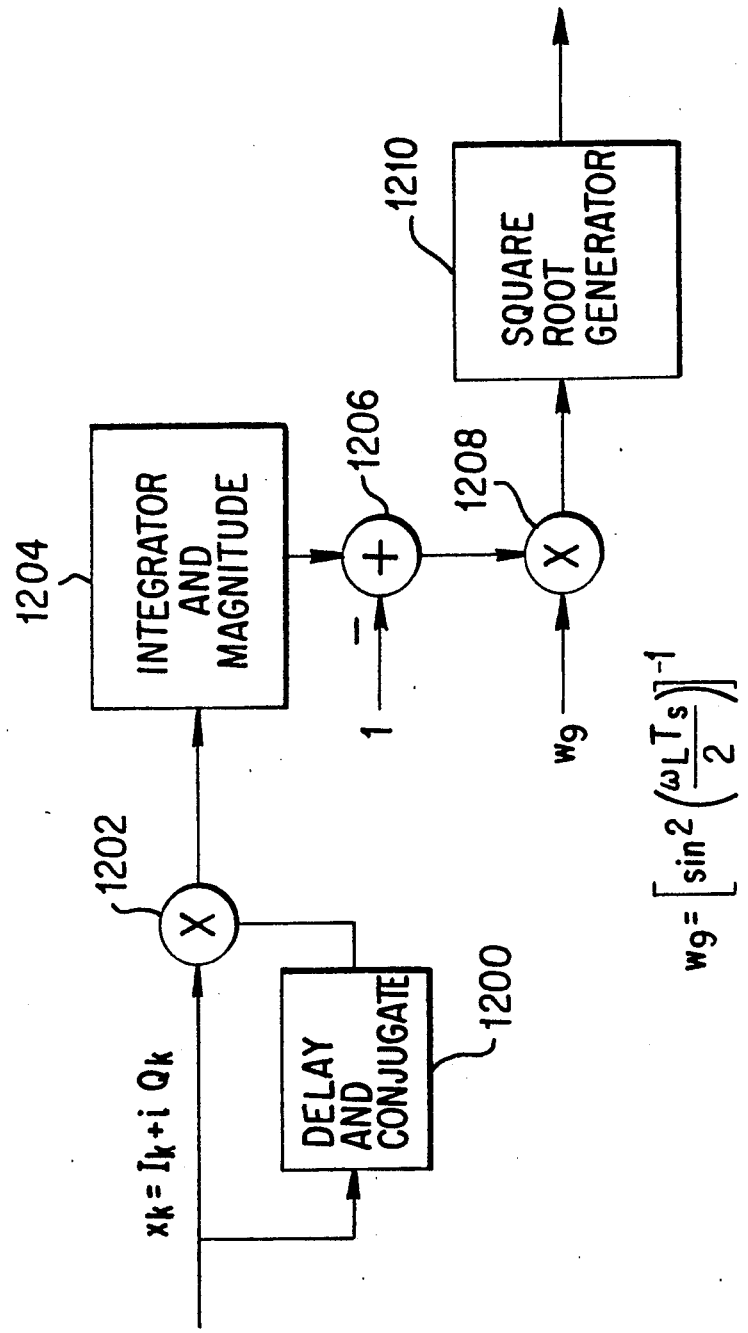
FIG. 12 is a schematic block diagram of the auto-correlation estimator circuitry which may be utilized in conjunction with the circuitry of FIG. 4.

FIG. 12 shows the use of the quadrature components $I_k$ and $Q_k$ in an auto-correlation process. When combined with the scale factor $W_9$, the output is the correlation estimate.

These, and their obvious modifications, are used to cover a wide range of beta and signal to noise ratios. The output of FIG. 3 is useful for a wide range of beta ($10^{-4}$ to $10^4$) and high SNR (up to 0 dB or more). The correlation estimate of FIG. 7, is useful in cases when beta<20. The phase estimators, FIGS. 5–10 are useful in the range of 0.03–3. The successive phase estimator is useful for 0.1<beta and for large beta. Each estimate can be used or not used depending on a prior knowledge of the range of beta (often maximum at the applied vibration source), and/or by "polling" the results to utilize the most stable output in a specific region of interest.

FIG. 5 shows the operation of the phase and co-phase signals estimation system which may be utilized in connection with the phase and co-phase estimation block 412.

As shown in FIG. 5, the quadrature signals $I_k$ and $Q_k$ are fed to delay circuits 500, 502, as well as to two multiplying circuits 504, 508. The outputs from the respective delay circuits 500, 502 are fed to two other multipliers 506, 510, as are the signals $I_k$ and $Q_k$, respectively. Additionally, the outputs from the two respective delay circuits 500, 502 are fed to the two multiplier circuits 508 and 504, respectively.

The output from the multiplier circuits 504–510 are fed respectively to the summing circuits 512, 516; 514, 518; 516, 512; and 518, 514. The outputs from the two adding circuits 512 and 514 are fed to an arctangent calculating circuit 520 which produces one of the output signals provided to both the vibration amplitude estimation block 416 and the vibration frequency estimation block 414. In a similar manner, the outputs from the two remaining adder circuits 516 and 518 are fed to a similar arctangent calculator circuit 522 to produce the second output from the phase and co-phase estimation block 412.

FIGS. 6–8 show additional circuitry for refining the output signals $\phi_k$ and $\phi'_k$ produced by the phase and co-phase estimation block 412 using, for example, the circuitry of FIG. 5. FIG. 6 shows a block diagram of additional phase processing circuitry.

The two signals output from the phase and co-phase estimation circuit 412 are fed to respective delay circuits 600, 602 as well as to respective adder circuits 604, 606 and 608, 610. In addition, the output signal produced by the delay 600 is fed to a first adder 604 and the output produced by the delay circuit 602 is fed to the first adder of the $\phi'_k$ signal 608.

The outputs from the respective adder circuits 604, 606, 608 and 610 are fed respectively to squaring circuits 612, 614, 616 and 618. Those squaring circuits respectively produce signals A–D which are utilized by the circuits of FIGS. 7 and 8.

FIG. 7 shows the successive-phase estimator circuitry which utilizes the signals A and B produced by the circuitry of FIG. 6 which are fed respectively to two multiplier circuits 700 and 702. Each of those multiplier circuits also receives as an input the signals $w_1$ and $w_2$, respectively, which represent scale factors, "constants" or "gains". The outputs from each of the multiplier circuits 700, 702 are added by the adder circuit 704 whose output is fed to a square root circuit 706. The output of the square root circuit 706 is the successive phase estimate.

FIG. 8 shows the circuitry which can be used to produce the successive co-phase estimator component, using the signals C and D from FIG. 6. Those signals are fed respectively to two multiplier circuits 800 and 802 which are also supplied with two scale factors signals $w_3$ and $w_4$, respectively. The outputs from the two multiplier circuits 800, 802 are added by the adder circuit 804 whose output is provided to a square root generator 806 which produces the successive co-phase estimate signal.

Instead of utilizing the circuitry of FIGS. 6–8 to further refine the output signals from the phase and co-phase estimation circuitry 412, the circuitry of FIG. 9, which implements the bi-phase estimator method, may be utilized. In that case, the two signals output from the phase and successive co-phase estimation circuit 412 are fed respectively to two multiplier circuits 900, 902. Those multiplier circuits are also fed with two scale factors signals $w_5$ and $w_6$, respectively. The outputs from the two multiplier circuits 900 and 902 are added by the adder circuit 904. The output from the adder circuit 904 is fed to a square root generator 906 whose output signal represents the bi-phase estimate.

FIG. 10 shows the circuitry for producing a 1-shift cross-phase value estimator for use with the circuitry of FIGS. 5–9. The signals $\phi'_k$ and $\phi_k$ fed to first and second multipliers 1000 and 1002. The outputs from those multipliers 1000, 1002 are fed to an adder circuit 1004 whose output is fed to a third multiplier circuit 1006. The third multiplier circuit 1006 is also fed with a signal $w_7$. The output from the multiplier 1006 is fed to a square root generator 1008 which produces the 1-shift cross-phase signal a its output.

FIG. 11 shows the circuitry for implementing the phase-ratio estimator for vibration frequency which utilizes as its input the signals $\phi_k$ — and $\phi'_k+$ from the circuitry of FIG. 6. The circuitry of FIG. 11 may be utilized as the vibration frequency estimation circuitry for element 414 of FIG. 4.

The two signals previously described are fed to a divider 1100. The output from the divider 1100 is fed to a square root generator 1102 which takes the square root of the results from the divider 1100 and applies it to an arctangent generator 1104. The output from the arctangent generator 1104 is fed to a multiplier 1106 which also receives the scale factor signal $w_8$. The output from the multiplier circuit 1106 represents an estimation of the internal vibration mode frequency and is fed to the vibration amplitude estimation circuitry 416 of FIG. 4.

FIG. 12 shows an auto-correlation estimator which may be used in connection with the circuitry of the present invention. FIG. 12 utilizes the number of ultrasound pulses, N, in order to estimate the auto-correlation and quasi-auto-correlation which can be varied to give the desired best combination of signal performance and frame rate. The choice of N also depends upon the vibration frequency of the applied external excitation.

The signal $x_k$ is applied to a delay and conjugate circuit 1200 as well as to a first multiplier 1202. The output from the delay and conjugate circuit 1200 is also applied to the multiplier 1202. The output from the multiplier 1202 is applied to an integrator and magnitude circuit 1204 whose output is fed to an adder circuit 1206. The signal unity or 1 is also fed to the adder 1206.

The output from the adder 1206 is fed to a second multiplier 1208 which also receives the scale factor signal $w_9$. The output from the multiplier circuit 1208 is fed to a square root generator 1210 which produces the desired correlation estimate signal.

FIGS. 13A and 13B show, respectively, how the teachings of the present invention can be applied to produce approximate estimations of vibration amplitude signals utilizing conventional velocity estimators (FIG. 13A) or conventional variance estimators (FIG. 13B).

Referring to FIG. 13A, a conventional velocity estimator 1300 is shown, which may, for example, be that of Kasai et al. or Pesque, both of which have been discussed previously herein. The output y(t) produced by the conventional velocity estimator 1300 is fed to both an integrator or differentiator 1302 and an adder 1306. The output from the integrator or differentiator 1302 is multiplied by a scale factor $w_{10}$. The output from the multiplier is added in the adder 1306 to the output from the conventional velocity estimator 1300. A square root generator 1308 produces the square root of the sum produced by the adder 1306, which is an approximate estimation of the vibration amplitude. It should be emphasized that the output from the square root generator 1308, while being more accurate than the output y(t) from the conventional velocity estimator 1300, is not nearly as accurate or precise as the output from the estimator systems disclosed herein.

FIG. 13B shows how the output from a conventional variance estimator 1310, such as that disclosed by Kasai et al., can be modified in order to produce a more accurate, although approximate estimation of vibration amplitude. The output from the conventional variance estimator 1310, v(t) is fed to an average and synchronize circuit 1312 and is then multiplied in a multiplier 1314 by a scale factor $w_{11}$. The output from the multiplier 1314 is the approximate estimation of the vibration amplitude.

As will be obvious to those of ordinary skill in the art, other variations of the present invention utilizing the time domain estimator methodology disclosed herein may be realized utilizing radio frequency signals (since there is a one-to-one correspondence between the baseband and RF signal processing), a combination of velocity, displacement, and/or acceleration estimators, or using spectral estimation techniques after those techniques have been adapted for estimating a truncated sinusoid on the phase or frequency estimates.

For example, a filter to eliminate unwanted signals, such as those from stationary targets, or those moving with slow steady (not vibrating) velocity, may be added. These are commonly referred to as "wall filters", "fixed echo suppressors" or "moving target indicators".

Additionally, commonly employed circuits could be added to suppress and not display estimation results when the received echoes are too weak or too strong. These are commonly referred to as "discriminator circuits", "squelch circuits" or "suppressor circuits".

Figure 14:
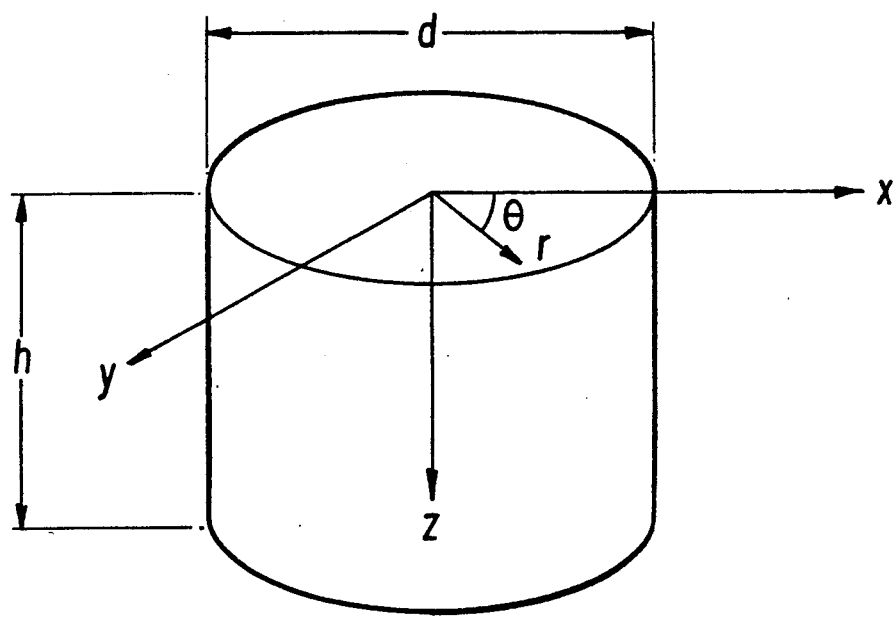
FIG. 14 is a diagram showing the geometry of a cylinder which is utilized in discussing the present method of breast imaging using modal vibration analysis.

As is known from the laws of basic mechanics and physics, an elastic material, when conformed to regular geometry such as a cylindrical, conical or planar shape, is capable of supporting standing waves, or vibration modes above a cutoff frequency. Those modal patterns depend upon the material constants, the boundary conditions and the applied vibration frequency. FIG. 14 shows a diagram for a cylindrical shape with rigid boundary conditions which is used for illustrative purposes with respect to the disclosed method of breast and tumor imaging.

The cylindrical shape of FIG. 14 can model a breast examination in which a rigid cylindrical-shaped cup is applied to gently conform the tissue and low amplitude low frequency vibration is applied at any surface by contact with an audio source. The rigid cup, together with the underlying muscle and rib cage, serve to enforce fixed boundary conditions. Similarly, conical or planar geometries can also be conformed to by a breast with minimal difficulty. The modal solutions in those cases have similar characteristics to the cylindrical case discussed below.

FIG. 14 shows a cylinder of diameter d and height h having rigid boundaries containing an elastic material with Lamé constants $\lambda$ and $\mu$. The constant is related to the bulk compressional property and the other constant is the shear modulus. They can be related to stiffness (Young's modulus) and Poisson's ratio in a known manner. For the case of a general linear isotropic and homogeneous material, by utilizing longitudinal and shear components which satisfy their own wave equations, and expressing the wave equations in cylindrical coordinates, the z-component of the displacement field can be obtained which is shown as equation (29) as $$\xi_z = \sum_{m,n,p} a_{m,n,p} \sin\left(\frac{\pi p z}{h}\right) J_m\left(\frac{r z_{m,n}}{d/2}\right) e^{im\theta}, \quad (29)$$

$$m = 0, 1, 2, \ldots$$
$$n = 1, 2, 3, \ldots$$
$$p = 1, 2, 3, \ldots$$

where $J_m(\beta)$ is the mth order Bessel function of the first kind with argument beta, $z_{m,n}$ is the nth zero of the Bessel function $J_m(\beta)$ and $a_{m,n,p}$ are constants determined by the boundary conditions and excitation sources.

The first, second and last index describes the spatial distribution along the angular, radial and vertical directions, respectively. A specific eigenmode can be excited by tuning the vibration source to a single proper eigenfrequency, where the eigenfrequencies are related to the geometry by the following equation:

$$f_{m,n,p} = c\sqrt{\left(\frac{z_{m,n}}{\pi d}\right)^2 + \left(\frac{p}{2h}\right)^2} \quad (30)$$

Substituting the estimated longitudinal and shear sound speeds of soft tissues and the values of Bessel zeroes into equation (30), the low order eigenfrequencies of the longitudinal and shear waves are found to be around 1K-100 KHz and 10–1000 Hz, respectively, for typical breast tissue. At this frequency range, the apparent low order modal shapes are most likely the shear vibration modal patterns. Thus, the modal shapes reveal the shear properties of the tissues in contrast with conventional ultrasound techniques which reveal longitudinal high frequency properties.

In order to perform the real-time imaging of motion of sinusoidal steady state vibration and tissue, which is termed "sonoelasticity imaging", a conventional B-scan imaging instrument is utilized with Doppler estimation methods as discussed previously herein, and particularly as discussed in connection with FIG. 2. As disclosed herein, the conventional B-scan imaging instrument is specially constructed to operate with the peculiar frequency shifts obtained from oscillating targets.

By adapting a conventional color Doppler imaging instrument to generate sonoelasticity images, the usual B-scan image of tissue echoes is depicted in gray and white and a color overlay indicates the detection of vibration above a certain threshold.

Figure 15:
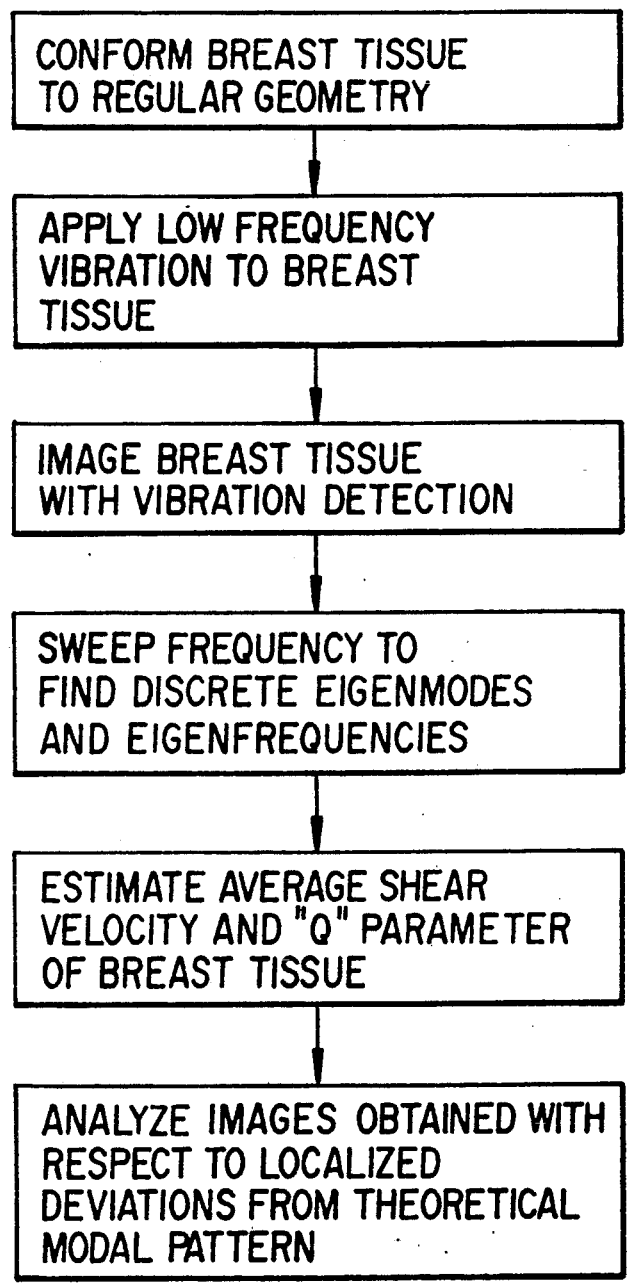
FIG. 15 is a block diagram showing a method of imaging breast tissue according to the present invention.

The method for characterizing breast tissue shown in FIG. 15 by modal vibration analysis disclosed herein utilizes the steps of conforming the breast to a regular geometry, such as the rigid cup discussed above in connection with FIG. 14, applying a low frequency vibration and imaging the conformed breast with conventional ultrasound with vibration detection, as discussed in connection with FIG. 2. The low frequency vibration is then swept in order to find discrete eigenmodes and eigenfrequencies.

The sweeping of the low frequency vibration preferably begins with the lowest frequency mode above the cutoff frequency. The average shear velocity and "Q" parameter of the bulk tissue is then estimated. Finally, the sonoelasticity images are analyzed with respect to localized deviations from the theoretical modal patterns. Such steps permit the quantitative and/or qualitative estimation of mechanical parameters which have been indirectly assessed by palpations but are not directly available from conventional or known imaging modalities.

The estimation of the average shear velocity and "Q" parameter of the bulk tissue is accomplished by the use of equation (30), which provides a relationship between the size and spacing of the modal patterns to the vibrational speed of sound. Thus, measurement of modal sizes can be accomplished through either direct placement of calibrated cursors, through sophisticated autocorrelation techniques or, preferably, through the transform techniques discussed herein.

When the vibration frequency is chosen to be an eigenfrequency of the tissue or organ, then a strong vibration amplitude response is measured within the tissue. The image of the eigenmode vibration pattern will have a dominant pattern spacing at the vibration wavelength. The Fourier transform of the image will therefore have a peak value at the spatial frequency corresponding to the vibration wavelength. This peak value can be measured from the Fourier transform of the sonoelastic image. The unknown speed of sound, c, can then be calculated as the product of the wavelength times the vibration frequency.

Those techniques give a value which is used to calculate a spatial or tissue average vibrational speed of sound for the tissue under study. The rate of change of the vibration amplitude with frequency, or the vibration response, is then measured over small excursions in frequency around the lower modal patterns. That provides a measure of the "Q" or viscosity component of the tissues under study. Those two parameters provide the bulk characterization of the tissue.

The general methodology of "sonoelasticity imaging" or Doppler vibration imaging discussed above is used here in a specific manner to produce vibration measurements and images of an organ. In the present application, the organ is shaped into a regular geometry; images are obtained at specific eigenfrequencies, determined as the locally maximum vibration response as vibration frequencies are slowly changed, and the sonoelasticity images are used to measure parameters which are used with equation (30) to produce quantitative estimates of the low frequency speed of sound of the tissue. Additionally, the "Q" or lossy nature of the tissue is estimated by observing the fall-off in vibration amplitude with small changes in vibration frequency around the lowest eigenmodes. In summary, the general methodology of the invention is directed towards the measurement and imaging of vibration. These measurements are used with the images to quantify the shear and longitudinal parameters of breast tissue and other organs.

The present method for analyzing breast tissue can also be used to detect lesions or tumors. It is known that the presence of a discrete inhomogeneity, that is, a stiff tumor, will alter the eigenfrequencies and eigenmodes of the tissue compared to the case in which no such inhomogeneity is present. The shift in eigenfrequencies is obtained by noting those frequencies which produce the highest amplitude vibration modes. Such frequencies are then compared as a left-right side control on the same individual, and, against a theoretical distribution expected from similar studies in which no lesions are present.

The exact location of the tumor is given by the appearance of a disturbance from the theoretical modal patterns. That can be detected visually, or using calculations which compare the image modal pattern against theoretical results. Filtering of the modal vibration image as based on the average size, shape and distance between modal patterns, can then be performed in the image or transform domains in order to enhance the visibility of any significant deviation.

Although only a preferred embodiment is specifically illustrated and described herein, it will be appreciated that many modifications and variations of the present invention are possible in light of the above teachings and within the purview of the appended claims without departing from the spirit and intended scope of the invention.

What is claimed is:

1. A method for determining the elastic constants of breast tissue in order to detect the presence of tumors or other abnormalities in said tissue using Doppler shifted signals reflected from said breast tissue, comprising the steps of:
   conforming the breast tissue to a predetermined regular geometry;
   exciting specific vibrational eigenmodes in said breast tissue;
   scanning said breast tissue with coherent radiation and receiving Doppler shifted signals reflected by said breast tissue; and
   analyzing said Doppler shifted signals to derive the vibration amplitude of said breast tissue.

2. The method of claim 1, wherein said step of analyzing includes analyzing an image created by exciting said specific vibrational eigenmodes in said breast tissue.

3. The method of claim 2, wherein said image has dominant pattern spacing at the wavelengths of said vibrational eigenmodes.

4. The method of claim 1, wherein said step of scanning uses pulsed coherent radiation.

5. The method of claim 1, wherein said step of analyzing comprises forming an image of the vibration amplitude within said conformed breast tissue and analyzing said image with respect to said specific vibrational eigenmodes in said breast tissue.

6. The method of claim 1, wherein said coherent radiation is pulsed electromagnetic radiation.

7. The method of claim 1, wherein said coherent radiation is acoustic radiation.

8. A method for characterizing breast tissue by modal vibration analysis in real-time, using Doppler shifted signals reflected from said breast tissue, comprising the steps of:
   conforming said breast tissue to a predetermined regular geometry;

vibrating said conformed breast tissue using a source of vibration;

impinging coherent radiation on the surface of said conformed breast tissue;

receiving said Doppler shifted signals reflected from said surface of breast tissue; and analyzing said Doppler shifted signals to determine discrete eigenmodes and eigenfrequencies.

9. The method of claim 8, further including the step of scanning the surface of said object with said impinging coherent radiation.

10. The method of claim 8, wherein said source of vibration has a frequency of approximately 1-1000 Hertz.

11. The method of claim 8, wherein said step of analyzing is accomplished using a time domain estimator system.

12. The method of claim 8, wherein said step of analyzing is accomplished using a frequency domain estimator system.

13. The method of claim 8, wherein said step of analyzing comprises the steps of:

generating quadrature phase signals representative of said Doppler shifted signals;

deriving the phase and co-phase signals of said quadrature phase signals; and calculating the vibration amplitude of said conformed breast tissue based upon said quadrature phase, phase and co-phase signals.

14. The method of claim 8, wherein said coherent radiation is pulsed electromagnetic radiation.

15. The method of claim 8, wherein said coherent radiation is acoustic radiation.

16. The method of claim 8, wherein said source of vibration produces one of pure tone and broad band signals.

17. A method for determining the elastic constants of soft tissue in order to detect the presence of tumors or other abnormalities in said tissue using Doppler shifted signals reflected from said soft tissue, comprising the steps of:

conforming the soft tissue to a predetermined regular geometry;

exciting specific vibrational eigenmodes in said soft tissue;

scanning said soft tissue with coherent radiation and receiving Doppler shifted signals reflected by said soft tissue; and analyzing said Doppler shifted signals to derive the vibration amplitude of said soft tissue.

18. The method of claim 17, wherein said step of analyzing includes analyzing an image created by exciting said specific vibrational eigenmodes in said soft tissue.

19. The method of claim 18, wherein said image has dominant pattern spacing at the wavelengths of said vibrational eigenmodes.

20. The method of claim 17, wherein said step of analyzing comprises forming an image of the vibration amplitude within said conformed soft tissue and analyzing said image with respect to said specific vibrational eigenmodes in said soft tissue.

21. The method of claim 17, wherein said step of scanning used pulsed content radiation.

22. The method of claim 17, wherein the step of analyzing comprises forming an image of the vibration amplitude within said conformed soft tissue and analyzing said image with respect to said specific vibrational eigenmodes in said soft tissue.

23. A method for characterizing soft tissue by modal vibration analysis in real-time, using Doppler shifted signals reflected from said soft tissue, comprising the steps of:

conforming said soft tissue to a predetermined regular geometry;

vibrating said conformed soft tissue using a source of vibration;

impinging coherent radiation on the surface of said conformed soft tissue;

receiving said doppler shifted signals reflected from said surface of soft tissue; and analyzing said doppler shifted signals to determine discrete eigenmodes and eigenfrequencies.

24. The method of claim 23, further including the step of scanning the surface of said soft tissue with said impinging coherent radiation.

25. The method of claim 23, wherein said source of vibration has a frequency of approximately 1-1000 Hertz.

26. The method of claim 23, wherein said step of analyzing is accomplished using a time domain estimator system.

27. The method of claim 23, wherein said step of analyzing is accomplished using a frequency domain estimator system.

28. The method of claim 23, wherein said step of analyzing comprises the steps of:

generating quadrature phase signals representative of said Doppler shifted signals;

deriving the phase and co-phase signals of said quadrature phase signals; and calculating the vibration amplitude of said conformed soft tissue based upon said quadrature phase, phase and co-phase signals.

29. The method of claim 23, wherein said coherent radiation is pulsed electromagnetic radiation.

30. The method of claim 23, wherein said source of vibration produces one of pure tone and broadband signals.

31. A system for characterizing breast tissue, comprising:

means for conforming said breast tissue into a predetermined geometry;

a vibration source for exciting vibrational eigenmodes in said breast tissue;

a pulsed coherent energy imaging system for scanning said breast tissue and for receiving Doppler shifted signals representative of said vibrational eigenmodes reflected by said breast tissue resulting from said scanning; and means for evaluating said vibrational eigenmodes occurring within said breast tissue.

32. The system of claim 31, wherein said vibration source produces one of pure tone and broadband signals.

* * * * *